US006878524B2

(12) United States Patent
Peng et al.

(10) Patent No.: US 6,878,524 B2
(45) Date of Patent: Apr. 12, 2005

(54) REAGENTS AND METHODS FOR DETECTION AND CHARACTERIZATION OF PROTEIN-PROTEIN INTERACTIONS, NUCLEAR EXPORT AND LOCALIZATION SEQUENCES AND INDUCIBLE GAL4P-MEDIATED GENE EXPRESSION IN YEAST

(76) Inventors: Gang Peng, 101 University Manor, Hershey, PA (US) 17033; James E. Hopper, 8 Foxglove Cir., Hershey, PA (US) 17033; Tamara Vyshkina, 4251 Round Top Rd., Elizabethtown, PA (US) 17022

( * ) Notice: Subject to any disclaimer, the term of this patent is extended or adjusted under 35 U.S.C. 154(b) by 0 days.

(21) Appl. No.: 10/165,873

(22) Filed: Jun. 10, 2002

(65) Prior Publication Data

US 2005/0048477 A1 Mar. 3, 2005

Related U.S. Application Data

(60) Provisional application No. 60/296,983, filed on Jun. 8, 2001.

(51) Int. Cl.$^7$ ............................................. G01N 33/53
(52) U.S. Cl. ............................... 435/7.1; 435/4; 435/6; 435/7.2
(58) Field of Search .......................... 435/4, 6, 7.1, 7.2

(56) References Cited

U.S. PATENT DOCUMENTS

| | | |
|---|---|---|
| 5,776,689 A | 7/1998 | Karin et al. |
| 6,083,693 A | 7/2000 | Nandabalan et al. |
| 6,303,310 B1 | 10/2001 | Lautar et al. |
| 6,342,345 B1 | 1/2002 | Blau et al. |
| 6,399,296 B1 | 6/2002 | Brent et al. |

OTHER PUBLICATIONS

Peng et al. PNAS 99:8548–8553.*
Alarcón, et al., Mol. Cell. Biol. 17:5968–5975.
Aronheim et al., 1997, Mol. Cell. Biol. 17:3094–3102.
Aronheim et al., 2000, Methods in Enzymology 328:47–58.
Biggar and Crabtree 2001, Embo J. 20:3167–3176.
Blank et al., 1997, Mol. Cell. Biol. 17:2566–2575.
Braunstein et al.1993, Genes Dev. 7:592–604.
Brent et al., 1985, Cell 43:729–736.
Brent et al., 1997, Annu. Rev. Genet. 31:663–704.
Buckholz, et al., 1981, Molec. Gen. Genet. 182:77–81.
Cagney et al., 2000, Methods in Enzymology 328(C):3–14.
Cardenas et al., 1995, Embo J. 14:2772–2783.
Chien et al., 1991, Proc. Natl. Acad. Sci. USA 88:9578–9582.
Cormack et al., Gene 173:33–38.
Devit et al., 1997, Mol. Biol. Cell 8:1603–1618.
Devit et al., 1999, Current Biol. 9:1231–1241.
Durfee et al., 1993, Genes and Dev. 7:555–569.
Fashena et al., 2000, Methods in Enzymology 328(C):14–26.
Fields and Song, 1989, Nature 340 :245–6.
Fujiki and Verner, 1993, J. Biol. Chem. 268:1914–20.
Funfschilling et al., 1999, Mol. Biol. Cell. 10:3289–99.
Gillen et al., 1992, J. Cell. Sci. 111:3235–44.
Golemis & Brent, 1992, Mol. Biol. Cell. 12:3006–3014.
Griffith et al., 1995, Cell 82:507–522.
Güldener et al., 1996, Nucleic Acids Research 24: 2519–2524.
Gyuris et al., 1993, Cell 75:791–803.
Huang, W., et al., 2001, Biotechniques 30:94–100.
Johnson et al., 1994, Annu. Rev. Biochem. 63:869–914.
Johnsson et al., 1994, Proc. Natl. Acad. Sci. USA 91:10340–10344.
Kino et al., 1987, J. Antibiot (Tokyo) 40:1249–1255.
Kokubo, et al., 1998, Mol. Cell. Biol. 189:1003–1012.
Kolanus, 1999, Curr. Top. Microbiol. Immunol. 243:37–54.
Kuras et al. 1999, Nature 399:609–613.
Laser et al., 2000, Proc. Natl. Acad. Sci. USA 97:13732–13737.
Lazo et al., 1977, Eur. J. Biochem. 77:375–382.
Le Douarin et al., 1995, Nucleic Acids Research 23:876–878.
Li et al., 1993, FASEB J. 7:957–963.
Liu et al., 1991, Cell 66:807–815.
Lohr et al., 1997 J. Biol. Chem. 262:15589–15597.
Marsolier et al., 1999, Methods and Enzymology 303:411–422.
McBride et al., 1992, J. Cell. Biol. 119:1451–1457.
Peng and Hopper, 2000, Mol. Cell Biol. 20:5140–5148.
Petitjean et al., 1990, Genetics 124:797–806.
Post–Beittenmiller, et al., Mol. Cell. Biol. 4:1238–1245.
Resh et al., 1999, Biochem. Biophys. Acta. 1451:1–16.
Serebriiskii et al., 1999, J. Biol. Chem. 274:17080–17087.
Serebriiskii et al., 2000, Biotechniques 28:328–336.
Sikorski and Hieter, 1989, Genetics 122:19–27.
Stagljar et al., 1998, Proc. Natl. Acad. Sci. USA 95:5187–5192.
Torchia et al., 1984, Mol. Cell Biol. 4:1521–1527.
Vidal et al., 1996, Proc. Natl. Acad. Sci. USA 93: 10315–20.
Vidal et al., 1996, Proc. Natl. Acad. Sci. USA 93: 10321–26.
Vojtek et al., 1993 Cell 74: 205–214.
Ward, 1990 Nucleic Acids Research 18: 5319.

\* cited by examiner

Primary Examiner—James Ketter
Assistant Examiner—David A. Lambertson
(74) Attorney, Agent, or Firm—McDonnell Boehnen Hulbert & Berghoff

(57) ABSTRACT

This invention provides methods for cytoplasmic detection of protein—protein interactions, nuclear export/localization sequences, and galactose-independent inducible Gal4p-mediated gene expression through the utilization of GAL regulatory factor, Gal80p, and the yeast galactose regulon.

22 Claims, 8 Drawing Sheets

A.

pGP74
acaacacactagtATGAATACAAACGTTCTAATATTCAGTTCTCCGGTCAGAGATTTACCAAGG
-657  -1
MetAsnThrAsnValLeuIlePheSerSerProValArgAspLeuProArg pGP144
acaacacactagtATGGGGTGTACAGTGAGTACCCAAACAATAGGAGACGAAAGTGATCCTTCT
-657  -1
MetGlyCysThrValSerThrGlnThrIleGlyAspGluSerAspProSer pGP147
caagctagtttgggctgcaggtcgactctagaggatccccgggtagtcATGAATACAAACGTT
-657  -2
MetAsnThrAsnVal

B.

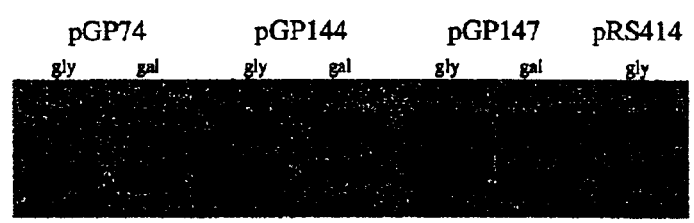

C.

|  | pGP74 | pGP144 | pGP147 |
|---|---|---|---|
| Gal3p expression level | 100 | 50 | 20 |
| α-galactosidase activity | 100±13 | 86±10 | 52±4 |

Fig. 2

A.
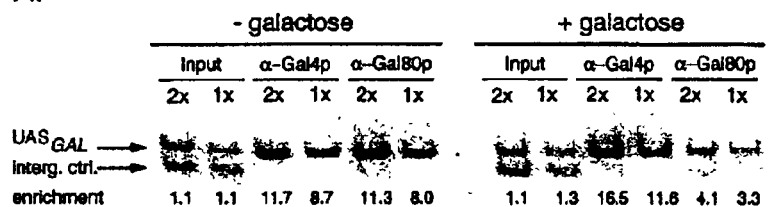
B.
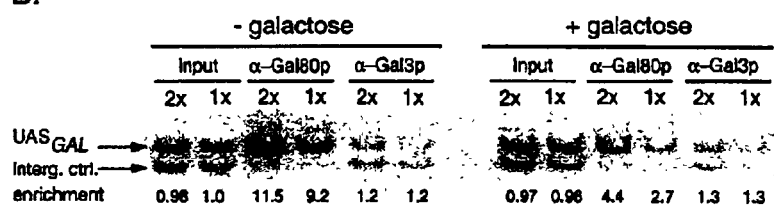
C.
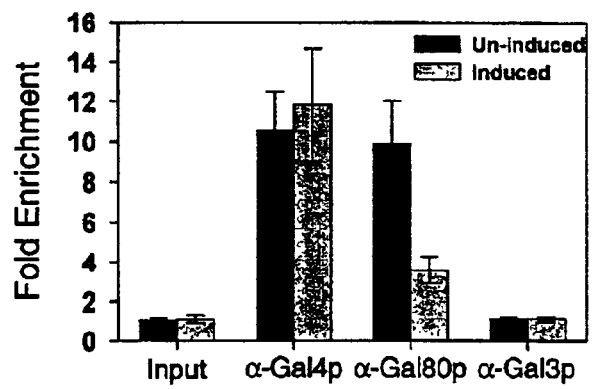
Fig. 3

A.
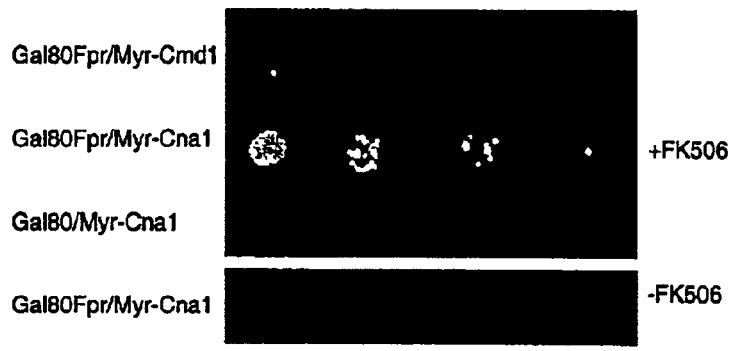
B.
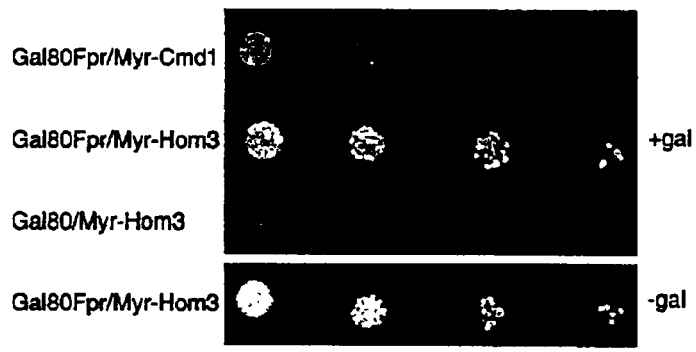
Fig. 4

SEQUENCE LISTING

<160> NUMBER OF SEQ ID NOS: 42

<210> SEQ ID NO 1
<211> LENGTH: 16
<212> TYPE: PRT
<213> ORGANISM: Artificial sequence
<220> FEATURE:
<223> OTHER INFORMATION: N-myristoylation signal

<400> SEQUENCE: 1

-continued

```
Met Gly Cys Thr Val Ser Thr Gln Thr Ile Gly Asp Glu Ser Asp Pro
1               5                   10                  15
```

<210> SEQ ID NO 2
<211> LENGTH: 16
<212> TYPE: PRT
<213> ORGANISM: Artificial sequence
<220> FEATURE:
<223> OTHER INFORMATION: N-myristoylation signal variant

<400> SEQUENCE: 2

```
Met Ala Cys Thr Val Ser Thr Gln Thr Ile Gly Asp Glu Ser Asp Pro
1               5                   10                  15
```

<210> SEQ ID NO 3
<211> LENGTH: 29
<212> TYPE: PRT
<213> ORGANISM: Artificial sequence
<220> FEATURE:
<223> OTHER INFORMATION: mitochondria outer membrane signal anchor

<400> SEQUENCE: 3

```
Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr
            20                  25
```

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 26
<212> TYPE: DNA
<213> ORGANISM: Artificial sequence
<220> FEATURE:
<223> OTHER INFORMATION: primer

<400> SEQUENCE: 7
aactgcaggt atgtctaaag gtgaag                                        26

<210> SEQ ID NO 8
<211> LENGTH: 59
<212> TYPE: DNA
<213> ORGANISM: Artificial sequence
<220> FEATURE:
<223> OTHER INFORMATION: primer

<400> SEQUENCE: 8
ctagtatggg gtgtacagtg agtacgcaaa caataggaga cgaaagtgat ccttctgca    59

<210> SEQ ID NO 9

-continued

```
<211> LENGTH: 51
<212> TYPE: DNA
<213> ORGANISM: Artificial sequence
<220> FEATURE:
<223> OTHER INFORMATION: primer

<400> SEQUENCE: 9
gaaggatcac tttcgtctcc tattgtttgc gtactcactg tacacccat a            51

<210> SEQ ID NO 10
<211> LENGTH: 48
<212> TYPE: DNA
<213> ORGANISM: Artificial sequence
<220> FEATURE:
<223> OTHER INFORMATION: primer

<400> SEQUENCE: 10
ctagtatgaa gagcttcatt acaaggaaca agacagccat tttggcaa               48

<210> SEQ ID NO 11
<211> LENGTH: 53
<212> TYPE: DNA
<213> ORGANISM: Artificial sequence
<220> FEATURE:
<223> OTHER INFORMATION: primer

<400> SEQUENCE: 11
ccgttgctgc tacaggtact gccatcggtg cctactatta ttacggtgct gca         53

<210> SEQ ID NO 12
<211> LENGTH: 51
<212> TYPE: DNA
<213> ORGANISM: Artificial sequence
<220> FEATURE:
<223> OTHER INFORMATION: primer

<400> SEQUENCE: 12
gcaacggttg ccaaaatggc tgtcttgttc cttgtaatga agctcttcat a           51

<210> SEQ ID NO 13
<211> LENGTH: 42
<212> TYPE: DNA
<213> ORGANISM: Artificial sequence
<220> FEATURE:
<223> OTHER INFORMATION: primer

<400> SEQUENCE: 13
gcaccgtaat aatagtaggc accgatggca gtacctgtag ca                     42

<210> SEQ ID NO 14
<211> LENGTH: 51
<212> TYPE: DNA
<213> ORGANISM: Artificial sequence
<220> FEATURE:
<223> OTHER INFORMATION: primer

<400> SEQUENCE: 14
cagttgggtg gtggtggtcg ttacccatac gacgtcccag actacgctgc a           51

<210> SEQ ID NO 15
<211> LENGTH: 51
<212> TYPE: DNA
<213> ORGANISM: Artificial sequence
<220> FEATURE:
<223> OTHER INFORMATION: primer

<400> SEQUENCE: 15
```

-continued gcgtagtctg ggacgtcgta tgggtaacga ccaccaccac ccaactgtgc a        51

<210> SEQ ID NO 16
<211> LENGTH: 29
<212> TYPE: DNA
<213> ORGANISM: Artificial sequence
<220> FEATURE:
<223> OTHER INFORMATION: primer

<400> SEQUENCE: 16
aactgcagat ttgtacaatt catccatac        29

<210> SEQ ID NO 17
<211> LENGTH: 27
<212> TYPE: DNA
<213> ORGANISM: Artificial sequence
<220> FEATURE:
<223> OTHER INFORMATION: primer

<400> SEQUENCE: 17
catggcatta ccaccatata catatcc        27

<210> SEQ ID NO 18
<211> LENGTH: 26
<212> TYPE: DNA
<213> ORGANISM: Artificial sequence
<220> FEATURE:
<223> OTHER INFORMATION: primer

<400> SEQUENCE: 18
gaaggtttgt ggggccaggt tactgc        26

<210> SEQ ID NO 19
<211> LENGTH: 22
<212> TYPE: DNA
<213> ORGANISM: Artificial sequence
<220> FEATURE:
<223> OTHER INFORMATION: primer

<400> SEQUENCE: 19
gtgcatttgg ccttcaatga gc        22

<210> SEQ ID NO 20
<211> LENGTH: 25
<212> TYPE: DNA
<213> ORGANISM: Artificial sequence
<220> FEATURE:
<223> OTHER INFORMATION: primer

<400> SEQUENCE: 20
aagtgatgtt cgacatacct gtaac        25

<210> SEQ ID NO 21
<211> LENGTH: 36
<212> TYPE: DNA
<213> ORGANISM: Artificial sequence
<220> FEATURE:
<223> OTHER INFORMATION: primer

<400> SEQUENCE: 21
cgttacccat acgacgtccc agactacgct ggttgg        36

<210> SEQ ID NO 22
<211> LENGTH: 36
<212> TYPE: DNA

```
<213> ORGANISM: Artificial sequence
<220> FEATURE:
<223> OTHER INFORMATION: primer

<400> SEQUENCE: 22
cgccaaccag cgtagtctgg gacgtcgtat gggtaa                           36

<210> SEQ ID NO 23
<211> LENGTH: 25
<212> TYPE: DNA
<213> ORGANISM: Artificial sequence
<220> FEATURE:
<223> OTHER INFORMATION: primer

<400> SEQUENCE: 23
gatacttccc aattcgtctt cagag                                      25

<210> SEQ ID NO 24
<211> LENGTH: 32
<212> TYPE: DNA
<213> ORGANISM: Artificial sequence
<220> FEATURE:
<223> OTHER INFORMATION: primer

<400> SEQUENCE: 24
ctggaataga ctagttgtgt attacgatat ag                              32

<210> SEQ ID NO 25
<211> LENGTH: 37
<212> TYPE: DNA
<213> ORGANISM: Artificial sequence
<220> FEATURE:
<223> OTHER INFORMATION: primer

<400> SEQUENCE: 25
ccaatgcatg tatgagtaaa ggagaagaac ttttcac                         37

<210> SEQ ID NO 26
<211> LENGTH: 26
<212> TYPE: DNA
<213> ORGANISM: Artificial sequence
<220> FEATURE:
<223> OTHER INFORMATION: primer

<400> SEQUENCE: 26
tttgtattgc atgcggatcg gggatc                                     26

<210> SEQ ID NO 27
<211> LENGTH: 39
<212> TYPE: DNA
<213> ORGANISM: Artificial sequence
<220> FEATURE:
<223> OTHER INFORMATION: primer

<400> SEQUENCE: 27
acaagtaata atcgatcgtc tgaagtaatt gaaggtaac                       39

<210> SEQ ID NO 28
<211> LENGTH: 35
<212> TYPE: DNA
<213> ORGANISM: Artificial sequence
<220> FEATURE:
<223> OTHER INFORMATION: primer

<400> SEQUENCE: 28
tttgctttta atcgattgtt gaccttcaac aattc                           35
```

<210> SEQ ID NO 29
<211> LENGTH: 64
<212> TYPE: DNA
<213> ORGANISM: Artificial sequence
<220> FEATURE:
<223> OTHER INFORMATION: primer

<400> SEQUENCE: 29
ataaactcgt gaaagcttaa agtaaggcct ttcacctaaa ctcgagtcgt tagaacgcgg    60
ctac                                                                64

<210> SEQ ID NO 30
<211> LENGTH: 66
<212> TYPE: DNA
<213> ORGANISM: Artificial sequence
<220> FEATURE:
<223> OTHER INFORMATION: primer

<400> SEQUENCE: 30
tcaattaagg ctcagatact taccataaac ataaataaaa agcagtcact atagggagac    60
cggcag                                                              66

<210> SEQ ID NO 31
<211> LENGTH: 43
<212> TYPE: DNA
<213> ORGANISM: Artificial sequence
<220> FEATURE:
<223> OTHER INFORMATION: primer

<400> SEQUENCE: 31
tttaactttt acgcatgcaa atgccaatgg atttccaacc tac                     43

<210> SEQ ID NO 32
<211> LENGTH: 41
<212> TYPE: DNA
<213> ORGANISM: Artificial sequence
<220> FEATURE:
<223> OTHER INFORMATION: primer

<400> SEQUENCE: 32
ggtggattta ggcgcctaat tccaagtctt ttcaattgtt c                       41

<210> SEQ ID NO 33
<211> LENGTH: 40
<212> TYPE: DNA
<213> ORGANISM: Artificial sequence
<220> FEATURE:
<223> OTHER INFORMATION: primer

<400> SEQUENCE: 33
caacgccagc atgctgtcga aagacttgaa ttcttcacgc                         40

<210> SEQ ID NO 34
<211> LENGTH: 40
<212> TYPE: DNA
<213> ORGANISM: Artificial sequence
<220> FEATURE:
<223> OTHER INFORMATION: primer

<400> SEQUENCE: 34
gtgcttagat cgattacgtt tcattcaaac cttcagtccc                         40

<210> SEQ ID NO 35

```
<211> LENGTH: 41
<212> TYPE: DNA
<213> ORGANISM: Artificial sequence
<220> FEATURE:
<223> OTHER INFORMATION: primer

<400> SEQUENCE: 35
aaaaaagtac agcatgcaaa tgtcctccaa tcttaccgaa g                    41

<210> SEQ ID NO 36
<211> LENGTH: 41
<212> TYPE: DNA
<213> ORGANISM: Artificial sequence
<220> FEATURE:
<223> OTHER INFORMATION: primer

<400> SEQUENCE: 36
gatgcaccta atcgattttt agataacaaa gcagcgaatt g                    41

<210> SEQ ID NO 37
<211> LENGTH: 64
<212> TYPE: DNA
<213> ORGANISM: Artificial sequence
<220> FEATURE:
<223> OTHER INFORMATION: pGP74 plasmid portion

<400> SEQUENCE: 37
acaacacact agtatgaata caaacgttct aatattcagt tctccggtca gagatttacc    60
aagg                                                                64

<210> SEQ ID NO 38
<211> LENGTH: 64
<212> TYPE: DNA
<213> ORGANISM: Artificial sequence
<220> FEATURE:
<223> OTHER INFORMATION: pGP144 plasmid portion

<400> SEQUENCE: 38
acaacacact agtatggggt gtacagtgag tacgcaaaca ataggagacg aaagtgatcc    60
ttct                                                                64

<210> SEQ ID NO 39
<211> LENGTH: 65
<212> TYPE: DNA
<213> ORGANISM: Artificial sequence
<220> FEATURE:
<223> OTHER INFORMATION: pGP147 plasmid  portion

<400> SEQUENCE: 39
caagctagct tgggctgcag gtcgactcta gaggatcccc gggcgagctc atgaatacaa    60
acgtt                                                                65

<210> SEQ ID NO 40
<211> LENGTH: 17
<212> TYPE: PRT
<213> ORGANISM: Artificial sequence
<220> FEATURE:
<223> OTHER INFORMATION: coding sequence for pGP74 plasmid

<400> SEQUENCE: 40

Met Asn Thr Asn Val Leu Ile Phe Ser Ser Pro Val Arg Asp Leu Pro
 1               5                  10                  15

Arg
```

```
<210> SEQ ID NO 41
<211> LENGTH: 17
<212> TYPE: PRT
<213> ORGANISM: Artificial sequence
<220> FEATURE:
<223> OTHER INFORMATION: coding sequence for pGP144 plasmid

<400> SEQUENCE: 41

Met Gly Cys Thr Val Ser Thr Gln Thr Ile Gly Asp Glu Ser Asp Pro
1               5                   10                  15

Ser

<210> SEQ ID NO 42
<211> LENGTH: 5
<212> TYPE: PRT
<213> ORGANISM: Artificial sequence
<220> FEATURE:
<223> OTHER INFORMATION: coding sequence for pGP147 plasmid

<400> SEQUENCE: 42

Met Asn Thr Asn Val
1               5
```

REAGENTS AND METHODS FOR DETECTION AND CHARACTERIZATION OF PROTEIN-PROTEIN INTERACTIONS, NUCLEAR EXPORT AND LOCALIZATION SEQUENCES AND INDUCIBLE GAL4P-MEDIATED GENE EXPRESSION IN YEAST

This application claims priority to U.S. provisional application Ser. No. 60/296,983, filed Jun. 8, 2001.

This application was supported by a grant from the National Institutes of Health, No. GM 27925. The government may have certain rights in this invention.

BACKGROUND OF THE INVENTION

1. Field of the Invention

This invention relates to interactions between biological molecules, particularly proteins, and methods for detecting and quantifying said interactions. The invention is particularly related to detection of protein—protein interactions that occur in the cellular cytoplasm. The invention specifically provides methods and reagents for detecting said cytoplasmic protein—protein interactions using a GAL regulatory factor in yeast, Gal80p, and the yeast galactose regulon. The invention further provides methods for the detection of nuclear export sequences and nuclear localization sequences. This invention also relates to the inducible production of proteins from GAL gene promoters without requiring galactose as the inducing molecule. The invention specifically provides methods and reagents for inducing Gal4p-mediated GAL gene promoter expression by small molecules other than galactose.

2. Background of the Related Art

The Human Genome Project has recently revealed the complete human genetic sequence. From studies on only a very small fraction of the genome (likely less than 0.1%), it appears that protein—protein interactions most often comprise key mechanistic features of biological processes. Protein—protein interactions thus provide potential targets for therapeutic intervention in many disease states. One method known in the art for detecting protein—protein interaction is the yeast two-hybrid system (Fields and Song, 1989, *Nature* 340: 245–6; Chien et al., 1991, *Proc. Natl. Acad. Sci. USA* 88: 9578–9582). This system is a powerful tool for genetic detection and isolation of yeast cells that harbor cDNA clones encoding interacting proteins. The two-hybrid system permits one to isolate from complex cDNA libraries a single cDNA encoding a protein, referred to as the prey, that interacts with a known protein, termed the bait. Moreover, by use of certain two-hybrid reporter assays one can genetically select for loss-of-interaction mutations in either of the corresponding cDNAs (i.e., either bait or prey). This last feature, incorporated into so called reverse two-hybrid selection protocols (Vidal et al., 1996, *Proc. Natl. Acad. Sci. USA* 93: 10315–20; Vidal et al., 1996, *Proc. Natl. Acad. Sci. USA* 93: 10321–26), provides an elegant, powerful and facile means of mapping amino acid determinants of interaction for each of the interacting proteins.

The classical two-hybrid method and derivatives (Durfee et al., 1993, *Genes and Dev.* 7: 555–569; Gyuris et al., 1993, *Cell* 75: 791–803; Vojtek et al., 1993 *Cell* 74: 205–214; Le Douarin et al., 1995, *Nucleic Acids Research* 23: 876–878; Brent et al., 1997, Annu. Rev. Genet. 31: 663–704; Kolanus, 1999, *Curr. Top. Microbiol. Immunol.* 243: 37–54; Cagney et al., 2000, *Methods in Enzymology* 328(C): 3–14; Fashena et al., 2000, *Methods in Enzymology* 328(C): 14–26) utilize a bait protein fused to a site-specific DNA binding domain and prey proteins fused to a transcriptional activation domain. Bait-prey interaction at the DNA site located within the promoter region of a reporter gene in the yeast nucleus places the transcriptional activation domain in a position to recruit RNA polymerase II (PolII) to the promoter. Thus, the central feature of all of these methods is transcription activator reconstitution (TAR) for Pol II by the two-hybrid protein—protein interaction in the nucleus. Because protein—protein interaction is required to reconstitute the PolII complex on the promoter, expression of a Pol II transcription-dependent reporter gene permits detection of the protein—protein interaction in the host yeast cell.

The two-hybrid system is more sensitive than other techniques known in the art, and is capable of detecting interactions not detectable by other methods such as co-immunoprecipitation (Li et al., 1993, *FASEB J.* 7: 957–963). The sensitivity of the two-hybrid system is likely due to the fact that transient interactions are sufficient to trigger a small amount of transcription resulting in mRNAs that undergo repeated rounds of translation. This results in a first amplification step (transcription) followed by a second signal output amplification step (translation) when the relatively stable protein is produced. The protein produced catalytically produces the final product that is detected, for example, as yeast colony growth or detectable reporter gene expression resulting from the two-hybrid protein—protein interaction.

Despite this sensitivity, all of the highly similar RNA Polymerase II transcription activator reconstitution (Pol II TAR)-based two-hybrid methods have serious limitations. One serious limitation is that these methods are not at all useful for a very large number of proteins including, but not limited to, virtually all transcriptional activators, transcriptional repressors, RNA polymerase II components, components of the general (basal) transcription machinery (RNA polymerase-associated proteins; >70 proteins), and the very large number of proteins identified as being associated with chromatin or involved in chromatin remodeling. Conventional two-hybrid methods are unavailing in analyzing protein—protein interactions with such proteins because they can activate reporter genes through either direct binding to the RNA polymerase or through binding to other proteins that in turn bind to an RNA polymerase subunit. In addition, practice has shown that multiple proteins not known to be involved in transcription activation or repression mechanisms for Pol II promoters have been found to have intrinsic transcription activation activity in the two-hybrid assay. Consequently numerous proteins cannot be employed as bait for screening cDNA two-hybrid libraries using a Pol II TAR-based method.

Attempts to overcome this limitation have been made in the prior art. For example, a two-hybrid method based on reconstitution of a transcription activator for RNA polymerase III promoters has recently been developed (Marsolier et al., 1999, *Methods in Enzymology* 303: 411–422). This Pol III TAR-based two-hybrid method capitalizes on the fact that the transcription of yeast class III genes (which include SNR6, tRNA and 5S RNA genes) relies only on two general transcription factors: TFIIIB and TFIIIC. TFIIIC recognizes class III gene promoter elements and assembles TFIIID on the promoter, allowing TFIIIC to recruit RNA polymerase III, which transcribes the gene. The system is cumbersome, however, because it requires two DNA sites: the first one being the A site that specifies transcription initiation mediated by TFIIIB recruitment of RNA Pol III; and the second site being the native binding site for TFIIIC (or B site) located down stream beyond the coding region (for SNR6). This Pol III TAR-based method has not been adopted in the general research community due to its cumbersome features and several additional limitations. Like the Pol II TAR-based method, bait and prey proteins must interact in the nucleus (see below). Only one reporter gene, the UASg-SNR6, is available, making it difficult to eliminate spurious false positives, for example due to mutations in the reporter gene itself. For quantifying the strength of the interaction in this system one must quantify the level of UASg-SNR6 transcripts by northern blots, which is a tedious assay compared, for example, to a colony growth assay.

Another serious limitation of the classical Pol II TAR-based system (and one that is not overcome using the Pol III-TAR based system) is that nuclear localization is required for TAR based two-hybrid methods. Perforce, a protein that normally never enters the nucleus and requires modification in the cytoplasm for proper activity (including binding activity) is not likely to participate in its normal protein interaction(s) if sequestered in the nucleus. For example, post-translational modification (such as phosphorylation) of cytoplasmic proteins is often mediated by interaction with one or more cytoplasmically-confined proteins; this process is illustrated in the many well-established membrane-based receptor signaling cascades. Such modifications would not occur (or would occur only very inefficiently) for proteins targeted to the nucleus in the Pol II and Pol III TAR-based two-hybrid systems known in the art. Thus, the Pol II TAR, Pol III TAR, and all other methods in the art requiring nuclear localization of bait and prey proteins are not useful for detecting protein—protein interactions in a significant fraction of cellular proteins.

Additionally, Pol II-based methods are hampered by a high frequency of false-positives (as shown in Chien et al., 1991, *Proc. Natl. Acad. Sci. USA* 88: 9578–9582; Brent et al., 1997, *Annu. Rev. Genet.* 31: 663–704; Serebriiskii et al., 1999, *J. Biol. Chem.* 274: 17080–17087; and Serebriiskii et al., 2000, *Biotechniques* 28: 328–336). It is expected that some of these false positives are a consequence of crowded conditions in the nucleus or in proximity to the chromatin, where the interaction must occur.

Two yeast two-hybrid methods not requiring nuclear localization of bait and prey proteins have been disclosed in the art: the split ubiquitin assay and hSos/Ras recruitment assay methods. The split ubiquitin assay utilizes the behavior of free (split) amino-terminal (N-terminal) and carboxyl-terminal (C-terminal) halves of ubiquitin, which can associate to form a native conformation that is specifically cleaved by ubiquitin-specific proteases (UBPs). The unassociated N-terminal or C-terminal half-molecules cannot be recognized or cleaved by the UBPs. In this system, cDNA encoding a bait protein is fused to cDNA encoding the N-terminus or the C-terminal half of a ubiquitin-reporter (R-URA3) fusion construct. Prey cDNA (or a multiplicity of prey library cDNAs) are fused to the N-terminus of the N-terminal half of ubiquitin. If no bait-prey interaction occurs in the cell, the URA3 enzyme (which is provided in fusion with the C-terminal half of ubiquitin) is catalytically active and confers growth-arrest on the cell in the presence of the suicide substrate analogue, 5-fluorotic acid (5-FOA). If bait-prey protein interaction does occur and brings the N-terminal and C-terminal halves of ubiquitin together in the correct steric orientation, cleavage by UBPs occurs, resulting in the URA3 enzyme being cleaved off and rapidly degraded by the N-end rule pathway. In the event of bait-prey interaction, consequently, no URA3 enzyme is present in the cell to convert 5-FOA to a toxic product, and the cells grow to form a detectable colony (see Johnsson et al., 1994, *Proc. Natl. Acad. Sci. USA* 91: 10340–10344; Stagler et al., 1998, *Proc. Natl. Acad. Sci. USA* 95: 5187–5192; and Laser et al., 2000, *Proc. Natl. Acad. Sci. USA* 97: 13732–13737).

The split-ubiquitin assay also has a number of serious limitations, however. One limitation is that the signal output (cell growth in the presence of the toxic precursor, 5-FOA) by which the interaction is detected is dependent on both the interaction of two proteins and a second kinetic step, cleavage of ubiquitin. This second, kinetic, step, is highly sensitive to steric effects arising from sub-optimal positioning or orientation of the N-terminal and C-terminal halves of ubiquitin. Because of the second step and its sensitivity to many factors, the signal output from the split-ubiquitin system cannot be a reliable indication of the strength (as opposed to the existence) of the protein—protein interaction. Weak signal output may be caused by strong interaction between the bait and prey that is unrecognized because of the lack of proportionality between the strength of the interaction and the strength of the signal generated. A second limitation is that any cDNA clones whose overexpression confers resistance to 5-FOA will be falsely identified as positive. It is known in the art that cDNAs encoding small molecule transporters are detected as false-positives because of their ability to confer resistance to 5-FOA (Laser et al., 2000, *Proc. Natl. Acad. Sci. USA* 97: 13732–13737). A third limitation results from the fact that at high local concentration the N-terminal and C-terminal halves of ubiquitin will associate with one another by themselves irrespective of bait and prey interaction. Thus, although the split-ubiquitin assay measures co-local concentrations of N-terminal and C-terminal halves of ubiquitin (conjugated with prey and bait proteins, respectively), detection is not necessarily a direct result of interaction between bait and prey proteins (Laser et al., 2000, *Proc. Natl. Acad. Sci USA* 97: 13732–13737). A fourth limitation of the split-ubiquitin method is its lack of signal amplification. A protein—protein interaction that orients the split halves of ubiquitin properly to be cleaved results in the degradation of one URA3 enzyme molecule. Additivity over multiple molecule degradations leads to protection of the cell from 5-FOA toxicity. There is no signal amplification (such as occurs in other two-hybrid systems, typically due to multiple rounds of translation of each mRNA molecule and multiple catalytic turnovers of the HIS3, URA3 or LacZ encoded enzymes in the Pol II- and Pol III-based methods described above). As a result, the split-ubiquitin assay is unlikely to be sensitive enough to detect weak protein—protein interactions that often drive important and dynamic biological processes.

The hSos-recruitment method utilizes hSos, the mammalian Ras guanyl nucleotide exchange factor (Ras GEF), that can complement a temperature sensitive yeast cdc25 mutant having a Ras protein that remains in the GDP-bound inactive form at 36° C. The yeast CDC25 gene encodes the yeast RasGEF (ySos) ortholog, and the cdc25 mutant RasGEF cannot activate Ras at the non-permissive temperature (36° C.). At that temperature the Ras signaling pathway is defective and the cells do not grow well. Introduction of hSos restores Ras pathway signaling and normal growth, providing that it is recruited to the yeast plasma membrane (the site of RasGEF activity). However, recruitment to the yeast membrane occurs only if a bait protein fused to hSos interacts with a membrane-localized prey protein.

In the performance of the hSos-recruitment method, prey proteins are fused to the Src myristoylation signal (Petitjean et al., 1990, *Genetic* 124: 797–806; Aronheim et al., 1997, *Mol. Cell. Biol.* 17: 3094–102; and Aronheim et al., 2000,

*Methods in Enzymology* 328: 47–58), resulting in membrane anchorage. In the practice of this method, a library of cDNAs fused to the v-Src myristoylation signal sequence (Myr) is used to transform a yeast host strain that bears the temperature sensitive cdc25-5 allele and is unable to grow well at 36° C.; an example of such a yeast strain is LRA26 (Petitjean et al., 1990, *Genetics* 124: 797–806). If LRA26 is transformed with a library plasmid encoding a Myr-fusion protein (prey) that interacts with the bait protein (bait-hSos fusion protein), the bait-hSos protein will be recruited to the membrane, resulting in restoration of Ras pathway signaling pathway and improved cell growth at 36° C.

Despite these features, the hSos/Ras recruitment assay itself has a very serious handicap: restoration of normal growth of the temperature-sensitive Ras mutant cells at 36° C. can occur in a great many ways other than via the desired protein—protein interaction. The resulting very high frequency of false positives is due to: 1) the high complexity of the Ras-cAMP signaling pathway downstream of the defective Ras step; and 2) selection of mammalian Ras family members when present on multi-copy plasmids (i.e., overexpressed) in yeast (Aronheim et al., 1997, *Mol. Cell. Biol.* 17: 3094–102). Multiple copies (i.e., overexpression) of some of the plurality of genes encoding Ras-cAMP pathway proteins, or the occurrence of recessive or dominant yeast chromosomal gene mutations in some of the corresponding genes produce false-positives by restoring normal growth of yeast Ras reactivation by hSos. These genes include the adenylate cyclase gene (CYR1), a suppressor of Ras mutation (CAP/SRV2), protein kinase A subunit genes (BCY1, TPK1, TPK2, or TPK3), cAMP-high and low affinity phosphodiesterases (PDE1 or PDE2), G-protein-coupled receptor system for glucose stimulation of cAMP synthesis (GPR1, GPR2) or any genes involved in signaling below Protein Kinase A.

This high background rate severely limits use of the hSos/Ras recruitment assay, if only because additional screening steps are required to identify false positives. In addition to false positives, the hSos/Ras CytoTrap system also produces a low number of independent colonies when used in a single library screening. The additional steps that have been incorporated to minimize these weaknesses add time and effort to the procedure (Huang, W., et al., 2001, *Biotechniques* 30: 94–100). An additional limitation of the hSos/Ras recruitment assay is the lack of a means of utilizing it in the reverse two-hybrid mode.

Given the above limitations of existing non Pol(II)TAR systems, there is a need in the art for systems that permit identification of cytoplasmic proteins that do not suffer from the intrinsic high background and false positive rates in these prior art methods. Considering the highly regulated nature of most important genes studied to date and the fact that the estimated number of protein-coding sequences in the human genome will be 40,000 to 80,000, it is important not to exclude a large fraction of genes from protein—protein interaction analyses, as occurs using the methods known in the art. In view of the large number of genetic sequences being determined, there is a need in the art for methods of identifying and characterizing the properties of the protein products encoded thereby.

SUMMARY OF THE INVENTION

The invention provides methods for detecting cytoplasmic protein—protein interactions and reagents for performing said methods. The invention provides a first fusion protein between a first protein or protein-binding fragment thereof and a transcription inhibitor that partitions or shuttles between the cell nucleus or cytoplasm, and a second fusion protein between a second protein or protein-binding fragment thereof and a cytoplasmic membrane localization factor. In a preferred embodiment, the cytoplasmic membrane localization factor is a cell membrane myristoylation signal or a mitochondrial membrane localization signal. The invention also provides a first recombinant expression construct encoding the first fusion protein and a second recombinant expression construct encoding the second fusion protein, as well as cells, most preferably yeast cells, comprising the first recombinant expression construct, the second recombinant expression construct and both said first and second recombinant expression constructs. In certain embodiments, said yeast cells also comprise a reporter gene transcribed from a promoter, wherein transcription from the promoter is sensitive to or regulated by inhibition by the transcription inhibitor comprising the first fusion protein.

In a preferred embodiment of the methods of the invention, termed "the 80-Trap" method herein, is provided a fusion protein comprising a yeast regulatory protein, Gal80p, a component of the galactose regulon comprising the GAL genetic switch that controls GAL gene expression in yeast. Gal80p is a nucleocytoplasm shuttling protein that can translocate from the cytoplasm to the nucleus and from the nucleus to the cytoplasm. In this embodiment of the methods of the invention, the first protein or protein-binding fragment thereof, termed "the bait," is fused to the Gal80 protein, while a second protein or protein-binding fragment thereof, termed "the prey," is targeted to either the cell plasma and vesicular membranes or the mitochondrial outer membrane by fusion with either cell membrane targeting and anchoring sequences or mitochondrial outer membrane targeting and anchoring sequences, respectively. Interaction between these two fusion proteins traps Gal80p in the cytoplasm, reducing the amount of Gal80p bound to the Gal4p transcription activation domain, and activates transcription from GAL promoters in the nucleus, inducing the expression of the GAL reporter genes. Accordingly, the interaction between bait and prey proteins in the 80-Trap method mimics the cytoplasmic interaction between Gal80p and Gal3p in the presence of galactose and traps Gal80p in the cytoplasm, resulting in insufficient Gal80p in the nucleus to inhibit Gal4p.

The invention in this embodiment provides a first recombinant expression construct encoding the first fusion ("bait") protein comprising the first protein or protein-binding fragment thereof fused to the Gal80 protein, and a second recombinant expression construct encoding the second fusion ("prey") protein comprising the second protein or protein-binding fragment thereof targeted to either the cell plasma and vesicular membranes or the mitochondrial outer membrane by fusion with either cell membrane targeting and anchoring sequences or mitochondrial outer membrane targeting and anchoring sequences, respectively. In this aspect are also provided cells, most preferably yeast cells, comprising the first recombinant expression construct, the second recombinant expression construct and both said first and second recombinant expression constructs.

The invention thus provides methods for introducing both said first and second recombinant expression constructs into a cell, most preferably a yeast cell, and expressing thereby the first and second fusion proteins therein. Expression of a second fusion protein that does not bind to the first fusion protein results in no increase in a gene operably linked to a promoter sensitive to or regulated by the transcription inhibitor comprising said first fusion protein. Expression of a second fusion protein that does bind to the first fusion protein results in an increase in a gene operably linked to a promoter sensitive to or regulated by the transcription inhibitor comprising said first fusion protein, because said first fusion protein partitions preferably to the cytoplasm and thereby releases transcription inhibition of said gene. In certain embodiments, said first fusion protein comprises a particular protein species. In alternative embodiments, said first fusion protein comprises a plurality of members of a cDNA library of species. In a preferred embodiment, said cell is a yeast cell. In particularly preferred embodiments, said transcription inhibitor is Gal80p.

This method permits screening for and characterization of protein interactions not possible using existing two-hybrid approaches. The method is advantageous for identifying protein interactions wherein one or both proteins is a transcriptional activator, transcriptional repressor, RNA polymerase II component, is a component of the general (basal) transcription machinery, or is one of more than the very large number of proteins identified as being associated with chromatin or involved in chromatin remodeling, including transcriptional repressors, and proteins requiring cytoplasmic modification for interaction. This method is also advantageous for identifying protein interactions where one or both proteins require residence in the cytoplasm for native activity. The capacity of the inventive methods for targeting prey to different cellular environments (plasma and vesicular membrane, outer mitochondrial membrane, and outer nuclear membrane and endoplasmic reticular membranes) are particularly advantageous in assays for certain protein interactions, such as for any proteins that have portions protruding into the cytoplasm. Additionally, semi-quantitative results comparing interactions between different protein pairs may be performed using the methods of this invention. Since Gal80p inhibits Gal4p-activated transcription from a multiplicity of yeast genes under the transcriptional control of GAL gene promoters, assay for expression of any one or combination of these genes, or exogenously-added reporter genes, reduces the number of false positive obtained during library screening. The method also takes advantage of a wide range of existing two-hybrid reporters known in the art, and can be used effectively in either the forward or reverse two-hybrid modes.

Thus, in a preferred embodiment the invention provides methods for detecting protein—protein interactions using the 80-trap method wherein the interaction is assayed by detection of expression of endogenous cellular genes transcribed by Gal4p. In alternative preferred embodiments, the invention provides methods for detecting protein—protein interactions using the 80-trap method wherein the interaction is assayed by detection of expression of a reporter gene transcribed by Gal4p. In these alternative embodiments, the cell, most preferably a yeast cell, further comprises a recombinant expression construct having a reporter gene operably linked to a Gal4p regulated promoter.

The invention also provides methods and reagents for detecting the presence of nuclear export sequences or nuclear localization sequences. In preferred embodiments of this aspect of the inventive methods, nuclear export sequences are detected by fusing a transcription inhibitor to a cDNA or to a plurality of members of a cDNA library. In a preferred embodiment, said transcription inhibitor is Gal80p. In this aspect, cDNAs encoding a peptide containing a nuclear export sequence (NES) sequester the transcription inhibitor, preferably Gal80p, to the cytoplasm. This in turn permits transcriptional activation of a gene operably linked to a promoter sensitive to or transcriptionally inhibited by the transcription inhibitor. In preferred embodiments, the promoter is a GAL gene promoter. In said preferred embodiments, the promoter is transcriptionally activated by Gal4p. In this embodiment, expression of the gene products, particularly reporter genes, are transcribed in the absence of galactose or other inducing agent. In additional preferred embodiments of this aspect of the inventive methods, nuclear localization sequences are detected by fusing a transcription inhibitor, preferably Gal80 p to a cDNA or to a plurality of members of a cDNA library. In addition, a GAL gene promoter is operably linked to a gene encoding an enzyme that converts a precursor molecule to a cytostatic or cytotoxic compound. In a preferred embodiment, the enzyme is URA3, and cells are plated on media containing galactose and the cytotoxic precursor compound, 5-fluorotic acid (5-FOA). In the absence of a NLS, sequester the transcription inhibitor, preferably Gal80p, is trapped in the cytoplasm permitting the expression of URA3 enzyme. URA3 converts 5-FOA into a toxic product and prevents cell growth. Conversely, when fused to an exogenous NLS, sequester the transcription inhibitor, preferably Gal80p, is sequestered in the nucleus and prevents transcriptional activation, most preferably by Gal4p, from activating URA3 expression, thus permitting cell growth. NLS sequences are thereby detected by detecting cell growth in the presence of galactose and 5-FOA.

In additional embodiments, the invention provides methods to induce Gal4p-mediated gene expression in the absence of galactose. In these aspects, cells, preferably yeast cells, are provided that harbor two fusion proteins that interact in response to the presence of an effector ligand. One of said interacting proteins, or protein-binding fragment thereof, is fused to Gal80p, and the second of said interacting proteins, or protein-binding fragment thereof, is fused to a membrane targeting sequence. The cells are treated with an effector ligand to induce protein—protein interaction. The association of the proteins traps Gal80p in the cytoplasm permitting the transcriptional activation of GAL gene promoters and the subsequent expression heterologous genes fused to those promoters. These methods permit activation of GAL regulated proteins by an effector ligand rather than by galactose. Advantageously, the effector ligand is a small molecule that is less costly than galactose, or that can trap Gal80p in the cytoplasm at lower concentrations than is required by galactose.

It is an advantage of the methods of this invention that they embody the ease, power and sensitivity of art-recognized Pol II TAR-based methods, but do not suffer from the exclusiveness and limitations of the Pol II TAR-based method. In addition, the methods disclosed herein are not expected to have high false positive rates, and are not cumbersome when put into practice. Unlike the Pol II TAR- and Pol II TAR-based systems known in the art, the inventive methods are not limited to detecting only protein—protein interactions that occur in the nucleus. In addition, the methods are easier to perform and measurement of protein—protein interactions more easily quantified than Pol III TAR methods. Neither do the inventive methods have the serious limitations imposed by the split-ubiquitin system discussed above.

Specific preferred embodiments of the present invention will become evident from the following more detailed description of certain preferred embodiments and the claims.

BRIEF DESCRIPTION OF THE DRAWINGS

FIG. 1A illustrates localization of Gal3p fused to green fluorescence protein (GFP) as visualized by fluorescence microscopy. Cells of yeast strain Sc781 (gal3Δ gal1Δ) carrying the indicated low-copy expression plasmid were grown to mid-log phase in medium containing 2% glycerol and 3% lactic acid as carbon source and induced with 2% galactose for 3 hours before microscopic observation. Green fluorescent protein (GFP) is inserted at the C termini of each of wild-type Gal3p, myristoylated Gal3p (Myr-Gal3p) and mMyr-Gal3p. The vacuolar (yeast lysosomal) membrane is readily seen in cells expressing Myr-Gal3GFP. For mitochondrial-associated Gal3p, the GFP sequence is positioned between the signal anchor sequence and the Gal3p sequence. Yeast mitochondria form the typical reticulum structure under the experiment conditions used. FIG. 1B shows MEL1 induction in cells carrying Gal3p derivatives. The results were obtained after 6 hours of galactose induction and were normalized to results obtained from cells carrying wild type Gal3p. The α-galactosidase induction assay was carried out essentially as described (Peng and Hopper, 2000, *Mol. Cell. Biol.* 20: 5140–5148). FIG. 1C shows membrane-associated Gal3p that sequesters Gal80p to membranes. Cells of yeast Sc786 strain (gal80Δ gal3Δ gal1Δ) carrying a low-copy plasmid expressing Gal80-GFP together with wild type Gal3p, or Myr-Gal3p, or mMyr-Gal3p, as indicated, were observed as in FIG. 1A. The images in FIG. 1C illustrate that Gal80-GFP molecules interact with membrane-associated Gal3p in galactose.

FIGS. 2A through 2C. Lowering Gal3p expression levels causes reduction in GAL gene expression. FIG. 2A shows sequence differences between different Gal3p encoding plasmids pGP74 (SEQ ID NO: 37), pGP144 (SEQ ID NO: 38) and pGP147 (SEQ ID NO: 39) with their respective amino acid coding sequences shown below (pGP74 coding region, SEQ ID NO: 40, pGP144 coding region, SEQ ID NO: 41, and pGP147 coding region, SEQ ID NO: 42). pGP74 (SEQ ID NO: 37) encodes a wild-type Gal3p expressed from an ADH2 promoter. pGP144 (SEQ ID NO: 38) encodes myristoylated Gal3p (Myr-Gal3p) expressed from an identical ADH2 promoter. pGP147 (SEQ ID NO: 39) encodes a wild-type Gal3p expressed from a modified ADH2 promoter containing a 50 bp sequence insertion between the promoter sequence and the start codon of Gal3p. Numbers in the promoter region correspond to the distance from the start codon in the ADH2 gene FIG. 2B illustrates results showing that different Gal3p expression levels were conferred by different Gal3p encoding plasmids. Protein extracts from cells grown in the absence of galactose and from cells grown for 6 hours in the presence of galactose were analyzed by Western blot. FIG. 2C shows MEL1 induction in cells carrying plasmids pGP74, pGP144 or pGP147. Cells carrying each of the respective plasmids were induced with 0.5% galactose for 6 hours and cellular extracts prepared. Aliquots of the cellular extracts were subjected to Western blot analyses as shown in FIG. 2B to provide estimates for Gal3p expression levels. The α-galactosidase induction assay was carried out essentially as described (Peng and Hopper, 2000, *Mol. Cell. Biol.* 20: 5140–8). Both Gal3p expression levels and MEL1 induction results were normalized to those of cells carrying pGP74.

FIG. 3A through 3C. Analysis of the association of Gal4p, Gal80p and Gal3p with $UAS_{GAL}$ sequences using chromatin immunoprecipitation. These data establish that galactose triggers a reduction of the amount of Gal80p bound to Gal4p at the $UAS_{GAL}$ site within GAL gene promoters. When considered with the illustration in FIG. 1C, these data establish that interaction of Gal3p and Gal80p in the cytoplasm leads to a reduction of Gal80p bound to Gal4p in the nucleus within the GAL gene promoters. Yeast cells were grown to early-log phase in medium containing 2% glycerol/3% lactic acid/0.05% glucose (–galactose, un-induced) and induced with 2% galactose for 20 minutes (+galactose, induced). The 344 bp PCR product ($UAS_{GAL}$) corresponds to the region extending from –600 to –257 relative to the +1 of the GAL1 gene. The 287 bp PCR product (interg. ctrl.) corresponds to an intergenic region located 5 Kb downstream from the GAL1 promoter and served as a control for background binding in the immunoprecipitation. The ratio between the 344 bp and 287 bp PCR products (fold enrichment) is calculated to normalize results and assess the promoter occupancy. FIG. 3A shows Gal4p and Gal80p occupancy at $UAS_{GAL}$ sites in un-induced and induced cells. The results from two-fold dilution of the template DNA used for the PCR reactions demonstrated that the reaction was within the linear range. Fold enrichments are indicated (enrichment). FIG. 3B shows Gal80p and Gal3p association with the $UAS_{GAL}$ region evaluated before and after galactose induction. FIG. 3C illustrates quantitation of promoter occupancy by Gal4p, Gal80p and Gal3p in un-induced and induced cells. Values are means (±standard deviation) of at least five experiments carried out with two sets of independently prepared chromatin samples.

FIGS. 4A and 4B. Surrogate protein—protein interaction activates GAL gene expression. FIG. 4A illustrates a small molecule other than galactose can be used to induce Gal4p mediated Gal promoter-mediated expression. FIG. 4A illustrates FK506-dependent HIS3 reporter expression. Gal80-Fpr1 designates the Gal80-Fpr1p fusion. Myr-Cna1 designates the plasma membrane targeted Cna1p. Myr-Cmd1 is a plasma membrane targeted calmodulin and is used as a control. The nutrient agar plates used here lacked histidine, tryptophan and uracil and contained 0.5% galactose/3% glycerol/2% lactic acid as carbon source. FK506 was used at 0.25 μg/mL where indicated. Identical results were obtained using nutrient agar lacking galactose (data not shown). FIG. 4B shows galactose-independent HIS3 reporter expression as a result of Gal80-Fpr1p and Myr-Hom3p interaction. The nutrient agar plate lacked histidine, tryptophan and uracil and contained 3% glycerol/2% lactic acid as carbon source. Galactose was used at 0.5% where indicated. The lack of tryptophan and uracil are required for selection and maintenance in yeast of the two plasmids Gal80-Fpr1p and Myr-Cna1p, and the lack of histidine is to provide a selective assay for the protein—protein interaction that activates the HIS3 reporter gene carried on a yeast chromosome.

DETAILED DESCRIPTION OF THE PREFERRED EMBODIMENTS

Figure 1:
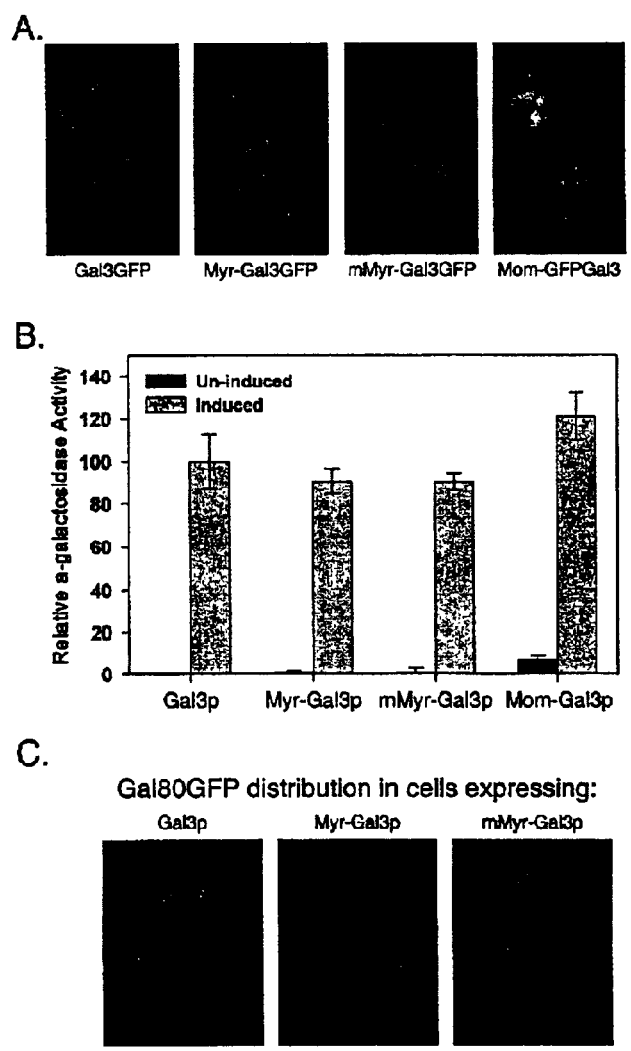
FIGS. 1A through 1C. Sequestration of Gal3p to cellular membranes does not affect its induction function. The results of assays performed as described in Example 1 establishes that Gal3p need not enter the yeast nucleus to mediate activation of Gal4p, and in turn, cause activation of Gal4p-activatable GAL gene promoters.
Figure 5:
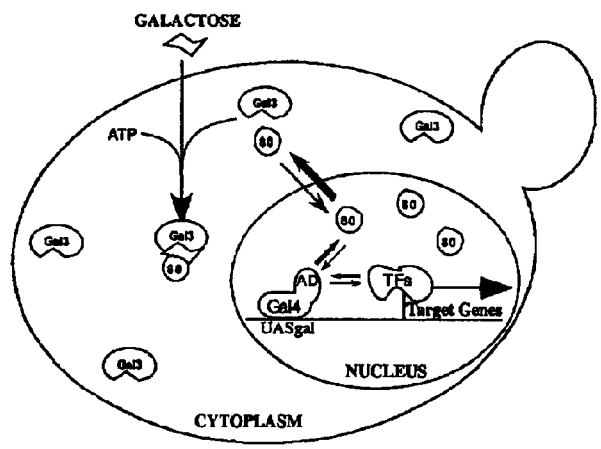
FIG. 5. Model for transcriptional regulation of GAL genes through modulation of protein—protein interactions in the nucleus and in the cytoplasm. Gal3p (Gal3) is located in the cytoplasm, while Gal80p (80) is located in both the cytoplasm and the nucleus and undergoes rapid nuclear-cytoplasmic shuttling. In the nucleus, a number of transcription factors (TFs) compete with Gal80p to bind to the activation domain (AD) of Gal4p. In the absence of galactose, binding of Gal80p to Gal4p effectively limited active transcription of GAL genes. Cellular uptake of galactose triggered Gal3p-Gal80p interaction in the cytoplasm and resulted in redistribution of Gal80p from the nucleus to the cytoplasm. These events led to a reduced probability of the binding between Gal80p and Gal4p. Subsequently, recruitment of chromatin remodeling factors and PolII holoenzyme activated GAL gene transcription.

All references, patents and patent applications are hereby incorporated by reference in their entirety.

According to the teachings of the specification, unless otherwise stated, the techniques utilized may be found in any of several references known in the art, including but not limited to: *Molecular Cloning: A Laboratory Manual, 3rd* ed. (Sambrook et al., 2001, MOLECULAR CLONING: A LABORATORY MANUAL, Cold Spring Harbor Laboratory Press: New York); *Gene Expression Technology* (Methods in Enzymology, Vol. 185, Goeddel, ed., Academic Press, San Diego, Calif., 1991); "Guide to Protein Purification" in *Methods in Enzymology* (Deutshcer, ed., (1990) Academic Press, Inc.); *PCR Protocols: A Guide to Methods and Applications* (Innis et al., 1990, Academic Press, San Diego, Calif.); *Culture of Animal Cells: A Manual of Basic Technique, 2nd* Ed. (Freshney, 1987, Liss, Inc. New York, N.Y.); *Gene Transfer and Expression Protocols*, pp. 109–128, Murray, ed., The Humana Press Inc., Clifton, N.J.), and the Promega 1996 Protocols and Applications Guide, 3rd Ed. (Promega, Madison, Wis.).

The present invention provides methods for detecting protein—protein interactions in the cytoplasm, detecting nuclear export/localization sequences, and regulating Gal4p-activation of GAL gene promoters by small molecules other than galactose.

The methods provided by this invention can be used with any transcriptional regulatory factors wherein the expression of a gene is mediated by a transcriptional activator that is in turn regulated by a nucleocytoplasmic transcriptional inhibitor. In the practice of the inventive methods, the bait protein is fused to any protein that functions as both a nucleocytoplasmic shuttling protein and an inhibitor or repressor of transcriptional activation. Localization of the transcriptional inhibitor/repressor to the nucleus prevents transcriptional activation by inhibiting the transcriptional activator or repressing recruitment of RNA polymerase. Conversely, localization of the transcriptional inhibitor to the cytoplasm permits transcriptional activator-mediated gene expression. Prey proteins are targeted to the cytoplasm, preferably by fusion to a cytoplasmic membrane localization sequence. Protein-protein interaction between the bait and prey proteins results in an imbalance in the kinetics or stoichiometry of nuclear/cytoplasmic partitioning of the transcription inhibitor in favor of the cytoplasm, thereby releasing transcription inhibition and increasing transcription of genes regulated by promoters sensitive to the inhibitor. In preferred embodiments, genes having increased transcription as a consequence of cytoplasmic localization of the transcription inhibitor are endogenous cellular genes or reporter genes operably linked to a promoter sensitive to the inhibitor. Said sensitivity is preferably mediated by the promoter being dependent on a transcription activator whose transcriptional activating activity is inhibited by the transcription inhibitor. The methods of the invention are provided to be used in the forward direction, i.e. detection of gene expression in the presence of protein—protein interactions, or the reverse direction, i.e. detection of loss of gene expression when said protein—protein interaction is inhibited or disrupted.

The invention provides a method for detecting protein—protein interactions in a host cell cytoplasm, the method comprising the steps of:

(i) introducing a gene expressing a first protein or protein-binding fragment thereof fused with the amino- or carboxyl-terminus of a transcriptional inhibitor;

(ii) introducing a gene expressing a second protein or protein-binding fragment thereof fused to a cytoplasm localization sequence, wherein upon interaction of the first and second proteins in the cell cytoplasm, said transcriptional inhibitor is localized to the cytoplasm, wherein transcription of a gene operably linked to a promoter that is sensitive to or regulated by said transcriptional inhibition is increased; and (iii) detecting said increased transcription of said gene wherein said protein—protein interaction is detected thereby.

In preferred embodiments, the cytoplasm localization sequence is a membrane targeting sequence, preferably a cell membrane targeting sequence or a mitochondrial membrane targeting sequence. Preferably, the cell is a yeast cell. In certain embodiments, the gene operably linked to a promoter that is sensitive to or regulated by said transcriptional inhibition is a exogenous reporter gene, most preferably encoding a detectable product or a product that produces a detectable metabolite. In other embodiments, the gene operably linked to a promoter that is sensitive to or regulated by said transcriptional inhibition is a exogenous reporter gene, most preferably encoding a detectable product or a product that produces a detectable metabolite.

As used herein, the term "operably linked" refers to components such as genetic components that are in a relationship, specifically covalently linked to one another, permitting them to function in their intended manner. For example, a control sequence "operably linked" to a protein coding sequence is ligated thereto so that expression of the protein coding sequence is achieved under conditions compatible with the transcriptional activity of the control sequences. In particular, a transcriptionally-regulated promoter such as a GAL promoter is covalently linked in an orientation, typically 5' to an open reading frame encoding an amino acid sequence of a protein, such as a reporter gene or a fusion protein of the invention, so that transcription of the coding sequence is appropriately regulated.

As used herein, the terms "fused" and "fusion protein" are intended to mean that the sequences, such as the amino acid sequences of the protein, are covalently linked to one another. When used with regard to nucleic acids encoding sad fusion protein, the term refers to covalent linkage of the sequences to be properly "in frame," so that translation of a mRNA encoding the fusion protein properly translates the individual components thereof in the proper reading frame of the genetic code.

As used herein, the term "protein binding fragments" is intended to encompass fragments of a protein involved in a protein—protein interaction that produces or is capable of producing a detectable signal according to the methods of the invention. Said fragments are capable of mediating the protein—protein interaction and are therefore necessary components of the fusion proteins of the invention. It will be recognized that other portions of the native protein involved in the protein—protein interactions assayed by the inventive methods may contribute to the interaction, but at least the portions termed "protein binding fragments" are required for the protein—protein interaction to take place.

In certain embodiments, the increased gene expression of the gene operably linked to a promoter that is sensitive to or regulated by said transcriptional inhibition is a selectable gene, wherein said increased transcription permits growth of the cell in selective conditions. In these embodiments, the inventive methods further comprise the steps of:

(iv) subjecting the host cell to selective growth conditions, and (v) detecting increased growth or survival of said cells under selective growth conditions, wherein said protein—protein interaction is detected thereby.

In alternative embodiments, the inventive methods provide a method for isolating a protein that is a member of an interacting protein pair, the method further comprising the step of:

isolating the encoding cDNA for said second protein.

In a preferred embodiment, termed the 80-Trap system, a specific bait protein (identified as a known protein of interest) is fused to Gal80p to create a fusion protein with Gal80 at either the amino- or carboxyl-terminus of Gal80p. The bait protein's binding partner, prey protein (either another known protein of interest or a multiplicity of yet unidentified potential partners encoded in a cDNA library), is tethered to the cell or mitochondrial membrane via fusion to membrane targeting sequences (for example, a myristoylation or mitochondrial Tom70 sequence, respectively), or one of a multiplicity of plasma membrane, vesicular membrane or mitochondrial outer membrane targeting sequences. If the bait and prey proteins interact in the cytoplasm, Gal80 is trapped in the cytoplasm and prevented from inhibiting Gal4p-mediated transcriptional activation of GAL gene promoters in the nucleus.

This invention is based, in part, on the discovery that Gal80p, which is an inhibitor of the transcriptional activator Gal4p, can be prevented from inhibiting Gal4p-mediated transcriptional activation of GAL gene promoters when Gal80p is trapped in the cytoplasm. Gal80p binds with high affinity to a specific portion of the Gal4p transcriptional activation domain, and blocks Gal4p's ability to recruit RNA polymerase II at $UAS_{GAL}$ sites contained in GAL gene promoters. In native yeast, Gal80p binding within the Gal4p transcriptional activation domain is relieved by the interaction between Gal3p and Gal80p, an interaction that occurs only in the presence of galactose. Normally Gal80p shuttles dynamically between the yeast nucleus and cytoplasm, and under steady state conditions in the absence of galactose a sufficiently high concentration of Gal80p is in the nucleus to bind to Gal4p and keep Gal4p inactive and the GAL regulon transcriptionally silent However, in the presence of galactose, Gal80p, binds to Gal3p molecules that are normally confined to the cytoplasm in native yeast cells, resulting in insufficient Gal80p in the nucleus to inhibit Gal4p. Consequently, Gal4p is able to activate genes of the galactose regulon, as well as reporter genes expressed via $UAS_{GAL}$ promoters. In additional embodiments, recombinant molecules consisting of the Gal4p transcription activation domain fused to the DNA-binding domain of other endogenous or exogenous DNA site-specific binding proteins. Using such constructs, reduced levels of Gal80p in the nucleus activate genes whose promoters contain the cognate binding site for the DNA-specific binding protein domain fused to the Gal4p transcription activation domain. For example, where LexA-Gal4 fusions are used (Golemis & Brent, 1992, *Mol. Cell. Biol.* 12: 3006–3014; Fashena et al., 2000, *Methods in Enzymology* 328: 14–27), the reporter genes that are activated in response to reduced levels of Gal80p in the nucleus are those that have the LexA operator site contained within the promoter of the said reporter genes (Golemis & Brent, 1992, *Id.*; Fashena et al., 2000, *Id.*). Said fusions comprise at least LexA repressor DNA binding domain (amino acids 1–87) or the entire LexA protein (amino acids 1–202, covalently linked to at least the N-terminus of the Gal4p activation domain (amino acids 768–881).

The system is designed to allow bait and prey fusions in either direction. Bait fusions can be done with Gal80p (termed "the B-80 version") or bait fusion can be done with either the myristoylation signal or the mitochondria outer membrane (MOM) targeting signal (B-Myr or B-MOM versions). The latter two embodiments have the advantage that libraries, which have prey fused to Gal80p (either N-terminal or C-terminal fusions to Gal80p) can be used with either the B-Myr or B-MOM versions of the desired bait.

In the B-80 version the protein of interest is fused with the Gal4p inhibitor, Gal80p. Gal80p functions as an inhibitor of Gal4p transcriptional activator and that this property is retained when other protein sequences are fused to either N- or C-terminus of Gal80p. This feature is an advantage in that it increases the chances that proteins fused to Gal80p to form a bait will not interfere with Gal80p's ability to inactivate Gal4p transcription activation activity. The invention provides libraries of either N-terminal or C-terminal fusions wherein the likelihood that bait proteins fused to Gal80p will fold in a manner that preserves native interacting surfaces is optimized.

For the protein to be tested or for cDNA libraries to be screened, cDNAs are preferably cloned into vectors encoding either the myristoylation signal or the mitochondria outer membrane-targeting signal. The ability to target proteins to different cellular environments (either the plasma membrane or mitochondrial outer membrane) provides utility for assays involving a protein that may require the particular environment of the cytoplasm or the environment proximal to a cellular membrane in the cytoplasm to be fully active and participate in its native interactions. Both vectors also provide the choice of including a green fluorescent protein (GFP) tag for convenient verification of protein expression and targeting.

In one aspect of this embodiment of the invention is provided a method for detecting protein—protein interactions that occur in a host cell cytoplasm comprising the steps of:

(i) introducing a gene expressing a first protein or protein-binding fragment thereof fused with the amino- or carboxyl-terminus of Gal80p;

(ii) introducing a gene expressing a second protein or protein-binding fragment thereof fused to a cytoplasm localization sequence, wherein upon interaction of the first and second proteins in the cell cytoplasm, said Gal80p fusion protein is localized to the cytoplasm, wherein transcription of a gene operably linked to a promoter that is sensitive to or regulated by said transcriptional inhibition is increased; and (iii) detecting said increased transcription of said gene wherein said protein—protein interaction is detected thereby.

In preferred embodiments, the cytoplasm localization sequence is a membrane targeting sequence, preferably a cell membrane targeting sequence or a mitochondrial membrane targeting sequence. Preferably, the cell is a yeast cell. In certain embodiments, the gene operably linked to a promoter that is sensitive to or regulated by Gal80p is an exogenous reporter gene, most preferably encoding a detectable product or a product that produces a detectable metabolite. In other embodiments, the gene operably linked to a promoter that is sensitive to or regulated by said Gal80p is a exogenous reporter gene, most preferably encoding a detectable product or a product that produces a detectable metabolite.

In certain embodiments, the increased gene expression of the gene operably linked to a promoter that is sensitive to or regulated by Gal80p is a selectable gene, wherein said increased transcription permits growth of the cell in selective conditions. In these embodiments, the inventive methods further comprise the steps of:

(vi) subjecting the host cell to selective growth conditions, and (vii) detecting increased growth or survival of said cells under selective growth conditions, wherein said protein—protein interaction is detected thereby.

In alternative embodiments, the inventive methods provide a method for isolating a protein that is a member of an interacting protein pair, the method further comprising the step of:

(viii) isolating the encoding cDNA for said second protein.

In a preferred embodiment, the first protein can be any protein that specifically interacts with another protein in a cell. In preferred embodiments, said first protein includes but is not limited to transcriptional proteins. As used herein the term "transcriptional protein" includes but is not limited to any protein that is involved with or a component of the transcriptional machinery of the cell, including transcriptional activators, transcriptional repressors, RNA polymerase II associated proteins, and chromatin associated proteins. In an additional embodiment, the first protein is encoded by a member of a cDNA library.

In a further embodiment, the second protein is any protein, preferably a protein encoded by a cloned cDNA. In a preferred embodiment, the second protein is encoded by a member of a cDNA library. In additional preferred embodiments, the second protein is fused to the C-terminus of a membrane targeting sequence. The term "membrane targeting sequence" is intended to encompass DNA sequences that result in membrane localization/anchorage of translated proteins. Membranes in this aspect of the invention include but are not limited to the cell membrane, mitochondrial outer membrane, nuclear membrane, vacuolar membranes, and all other organelle membranes. In a preferred embodiment, the second protein is localized to the cellular membrane via fusion to a myristoylation sequence. In an additional preferred embodiment, the second protein is localized to the outer mitochondrial membrane via fusion to a Tom70/Mas70sequence or any other mitochondrial outer membrane protein that protrudes into the cytoplasm.

In additional preferred embodiments, the invention provides methods wherein the yeast transcriptional repressors, Mig1p and Mig2p encoded by the MIG1 and MIG2 genes respectively (see, De Vit and Johnston, 1999, *Current Biol.* 9: 1231–41; De Vit et al., 1997, *Molec. Cell. Biol.* 8: 1603–18) are used. Mig1p is a repressor of transcription of glucose-repressed genes in yeast, and the subcellular localization of Mig1 is regulated by glucose. Mig1 is imported into the nucleus within minutes after the addition of glucose and is just as rapidly transported back to the cytoplasm when glucose is removed. Thus, Mig1 shuttles between nucleus and cytoplasm; and in the presence of glucose its nuclear localization is favored (and its target genes are repressed), whereas in the absence of glucose its cytoplasmic localization is favored (and its target genes can be expressed). Thus, if a bait protein is fused to Mig1p and binds to prey protein that is tethered to membranes outside the nucleus, then Mig1 should localize preferentially to the cytoplasm and allow the glucose-repressed genes to be expressed.

The invention also provides host cells harboring expression constructs described herein. "Expression constructs" and "recombinant expression constructs" will be understood to be genetically-engineered nucleic acid sequences encoding at a minimum an origin of replication, a selectable marker and a gene comprising a polypeptide-encoding nucleic acid that is expressed in a recipient host cell. In preferred embodiments, cDNAs and galactose regulon components described above are used in the construction of recombinant expression constructs. In additional preferred embodiments, cDNAs and glucose regulon components described above are used in the construction of recombinant expression constructs. The recombinant expression constructs of the invention most preferably encode transcription factors derived from the galactose regulon, most preferably Gal80p, and the glucose regulon, most preferably Mig1p and Mig2p. The recombinant expression constructs also comprise protein-encoding cDNAs fused to the amino- or carboxyl-terminal sequence of Gal80p or Mig1p. In a further embodiment, the recombinant expression constructs comprise protein-encoding cDNAs fused to membrane targeting peptides. In additional embodiments, the recombinant expression constructs encode membrane targeting signal peptides fused to protein-encoding cDNAs or a plurality of protein-encoding cDNAs in a cDNA libraries. In a preferred embodiment, the expression constructs further encode a myristoylation sequence or a Tom70/Mas70 membrane targeting sequence.

In a further embodiment, the invention provides a method for modulating fusion gene expression (inter alia, Gal80p fusion and membrane targeting fusions). One type of vector provides fusion protein expression driven by the full-length yeast ADH1 promoter, resulting in high level, constitutive expression. In embodiments wherein the fusion protein construct is found to be toxic to the cell, another type of vector providing expression driven by a full-length yeast ADH2 promoter is preferably used, wherein the protein is only expressed in absence of glucose in the culture media. The protein can be expressed at even lower levels from a modified yeast ADH2 promoter containing 50 bp of sequence insertion between the promoter sequence and the start codon. Alternatively, the protein can be expressed from the yeast SSN6 or TUP1 promoters or any of a multiplicity of yeast promoters that satisfy the requirement that the membrane-targeted protein is produced at levels sufficient to create a high number of potential binding sites outside the nucleus relative to the number of Gal80p fusions. Any of a multiplicity of yeast promoters can be used to drive expression of the Gal80p fusions so long as the promoter is weaker than the promoter chosen to drive expression of the membrane-targeted fusion protein.

In an additional embodiment, the invention provides methods for detecting protein—protein interactions.

In a further embodiment, the selectable growth conditions are chosen to select for yeast comprising a yeast selectable reporter gene that is expressed upon transcriptional activation of an upstream gene promoter having a LexA repressor binding site (Lex A operators; Golemis & Brent, 1992, *Id.*; Fashena et al., 2000, *Id.*; Brent & Ptashne, 1985, *Cell* 40: 729). In these embodiments, protein—protein interactions are determined by expression of selectable or detectable reporter genes, or subsequent growth of the host cell arising from expression of an endogenous GAL-regulated gene or a selectable reporter gene, or a combination thereof. In this embodiment, protein—protein interaction permits transcriptional activation and expression of a selectable or detectable reporter gene, or subsequent growth of the host cell arising from expression of an endogenous GAL-regulated gene or a selectable reporter gene, or a combination thereof. In the practice of one aspect of this embodiment of the invention, the selectable reporter gene or the selectable endogenous GAL-regulated gene must be expressed to high enough expression levels to provide sufficient production of the gene product to permit cell growth under selectable conditions. In a preferred embodiment, the selectable growth conditions are chosen to select for yeast comprising a yeast selectable reporter gene that is expressed upon transcriptional activation of an upstream GAL gene promoter having a UAS$_{GAL}$ DNA sequence. Any number of selectable or reporter genes may be utilized and include but are not limited to HIS3, ADE2, ADE5, ADE7, LYS2, LEU2, URA3, TRP1, KAN. In an additional preferred embodiment, the selectable reporter gene is HIS3.

In a further embodiment, the invention provides methods for detecting protein—protein interactions by expression of a detectable reporter gene. A reporter gene as used in these methods is any known in the art including but not limited to HIS3, ADE2, ADE5, ADE7, LYS2, LEU2, URA3, TRP1, KAN, green fluorescence protein (GFP), cyan fluorescence protein (CFP), beta-glucoronidase, luciferase, and lacZ (encoding beta-galactosidase). The detectable reporter gene or genes utilized may not be the same gene or genes utilized as the selectable reporter gene (gene required for growth). In another embodiment of this aspect of the inventive methods, protein—protein interaction is detected by reporter gene activity. Reporter gene activity may be determined by growth (i.e., using a selection protocol), or biochemical activity, or a biophysical signal such as fluorescence, photon emission, change in color spectrum, transfer of radioactive groups, or by binding to an antibody and detected either directly or indirectly, for example, by conjugation to a detectable marker such as horseradish peroxidase or a fluorescent agent.

The expression of all screenable or selectable reporter genes is dependent on the activation of upstream promoters having the required DNA site for binding the site-specific DNA-binding domain that is fused to the Gal4p transcription activation domain. This is dependent on the DNA site locating a transcription activator protein such as Gal4p or its transcription activation domain to the promoter. Where the native Gal4p is used, the expression of all screenable or selectable reporter genes is dependent on the activation of upstream GAL gene promoters having a UAS$_{GAL}$ DNA sequence that locates Gal4p to the promoter.

The tern "GAL gene promoter" is any regulatable promoter from any of the genes of the yeast galactose regulon including but not limited to GAL1, GAL7, GAL10, GAL2, GAL5, MEL1 and other native GAL gene promoters of indigenous to yeast as well as all artificial, man-made galactose-responsive promoters that are under the control of the GAL gene promoter specific UAS$_{GAL}$ sequences and the UAS$_{GAL}$-specific transcriptional activator, Gal4p or derivatives of Gal4p that retain the DNA binding domain and the Gal80p-binding domain of Gal4p. Alternatively, Gal4-activatable promoters having synthetic UAS$_{GAL}$ sites can be utilized to drive induced expression of polypeptides. The invention may also utilize native GAL gene promoters indigenous to yeast.

The term "detectable" refers herein to the ability to identify, measure, or localize a protein product, either antigenically, immunologically or enzymatically within the host cell or cell extracts. Protein products can further comprise additional sequences useful for promoting identification or purification of the protein, such as epitope or fluorescent tags. Examples of such epitope and fluorescent tags include, but are not limited to FLAG (Sigma Chemical, St. Louis, Mo.), myc (9E10) (Invitrogen, Carlsbad, Calif.), 6-His (Invitrogen; Novagen, Madison, Wis.), HA (Boehringer Manheim Biochemicals), green fluorescent protein (GFP), and cyan fluorescent protein (CFP). In one embodiment, polypeptide sequences, or fragments thereof, are operatively linked to a nucleic acid sequence encoding an "epitope tag", so that the protein is expressed with an epitope tag. The epitope tag may be expressed as the amino terminus, the carboxyl terminus, or internal to any of the polypeptide chains comprising any of said first protein second protein, or Gal80p so long as the resulting protein remains functional and is able to interact with other proteins.

The term "isolating" refers to any of the known methods in the art for the isolating or purifying DNA. Plasmids containing cDNAs of interest are isolated from yeast and transformed into *E. coli* for subsequent amplification, purification, and characterization. (Ward, 1990 *Nucleic Acids Research* 18: 5319). Such methods for isolation include but are not limited to PCR amplification, SDS-alkaline lysis, lithium chloride/Triton® X-100, resin-based isolation, and introduction into *E. coli*, restriction digestion, any other methods known in the art or any combination thereof.

The invention also provides a method for detecting in a host cell cytoplasm a nuclear export sequence (NES), the method comprising the steps of:
  a) introducing into the cell a recombinant expression construct encoding a NES-containing protein or NES-containing fragment thereof fused with the amino- or carboxyl-terminus of a transcription inhibitor;
  b) assaying the cell for expression of a gene operably linked to a promoter that is sensitive to or regulated by said transcriptional inhibition;

c) detecting increased expression of said gene;
wherein an NES is detected thereby.

In a preferred embodiment, the transcription inhibitor is Gal80p. In a preferred embodiment, the recombinant expression construct encodes a cDNA or a member of a cDNA library. Also preferred are methods wherein the gene operably linked to a promoter that is sensitive to or regulated by said transcriptional inhibition is a selectable gene, wherein increased expression of said gene confers a growth advantage on the cell. In these embodiments, the inventive methods further comprise the steps of:

d) subjecting the host cell to selective growth conditions, and e) detecting increased growth or survival of said cells under selective growth conditions, wherein said protein—protein interaction is detected thereby.

The invention also provides methods for isolating NES, the method comprising the steps of:

a) detecting increased expression of the gene operably linked to a promoter that is sensitive to or regulated by said transcriptional inhibition in a cell comprising a recombinant expression construct encoding a NES-containing protein or NES-containing fragment thereof fused with the amino- or carboxyl-terminus of a transcription inhibitor; and b) isolating said recombinant expression construct comprising said NES from the cell.

In preferred embodiments, the gene operably linked to a promoter that is sensitive to or regulated by said transcriptional inhibition is a gene expressed from an activated yeast GAL gene promoter. Said genes include but are not limited to HIS3, URA3, TRP1, ADE2, ADE5, ADE7, LYS2, KAN$^R$, or one of a multiplicity of genes whose encoded protein provides yeast the ability to grow under imposed selection conditions. Most preferably, the GAL gene promoter is a galactose-inducible UAS$_{GAL}$ promoter. In additional preferred embodiments, the gene operably linked to a promoter that is sensitive to or regulated by said transcriptional inhibition is an endogenous cellular gene, including but not limited to. GAL1, GAL7, GAL10, GAL5/PGM2, FUR4, GCY1, LAP3/GAL6, MTH1, PCL10 or MEL1. Also preferred are embodiments wherein gene operably linked to a promoter that is sensitive to or regulated by said transcriptional inhibition is an exogenous reporter gene encoding a detectable product. In further preferred embodiments, the gene operably linked to a promoter that is sensitive to or regulated by said transcriptional inhibition is a selectable gene, wherein increased expression of said gene confers a growth advantage on the cell. In these embodiments, the method further comprises the steps of:

a) subjecting the host cell to selective growth conditions, and b) detecting increased growth or survival of said cells under selective growth conditions, wherein said NES is detected thereby.

The NES can be isolated from a recombinant expression construct comprising a cell expressing a gene operably linked to a promoter that is sensitive to or regulated by said transcriptional inhibition.

In an additional preferred embodiment, the invention includes a method for the detection of proteins of fragments thereof containing nuclear export sequence (NES). cDNAs encoding proteins containing an NES sequence are fused to Gal80p. The presence of an exogenous nuclear export sequence in said protein results in sequestration of Gal80p in the cytoplasm and subsequent activation of GAL promoter-linked reporter gene expression.

The invention also provides a method for detecting a nuclear localization sequence (NLS) in a host cell comprising the steps of.

a) introducing into the cell a recombinant expression construct encoding a NLS-containing protein or NLS-containing fragment thereof fused with the amino- or carboxyl-terminus of a transcription inhibitor;

b) assaying the cell for expression of a gene operably linked to a promoter that is sensitive to or regulated by said transcriptional inhibition;

c) detecting decreased expression of said gene;
wherein an NLS is detected thereby.

In a preferred embodiment, the recombinant expression construct encodes a cDNA or a member of a cDNA library. Also preferred are methods wherein the gene operably linked to a promoter that is sensitive to or regulated by said transcriptional inhibition encodes a product that converts a non-toxic compound to a cytotoxic or cytostatic compound. In additional preferred embodiments, expression of the gene operably linked to a promoter that is sensitive to or regulated by said transcriptional inhibition is inducible when the cell is contacted with an inducing agent. In preferred embodiments, the gene operably linked to a promoter that is sensitive to or regulated by said transcriptional inhibition encodes a product that converts a non-toxic compound to a cytotoxic or cytostatic compound and wherein expression of the gene operably linked to a promoter that is sensitive to or regulated by said transcriptional inhibition is inducible when the cell is contacted with an inducing agent, wherein decreased expression of said gene is detected by cell growth or survival when the cell is contacted with both the inducing agent and the cytotoxic or cytostatic compound.

The invention also provides methods for isolating NLS, the method comprising the steps of:

a) detecting decreased expression of the gene operably linked to a promoter that is sensitive to or regulated by said transcriptional inhibition and encoded by a recombinant expression construct encoding a NLS-containing protein or NLS-containing fragment thereof fused with the amino- or carboxyl-terminus of a transcription inhibitor; and b) isolating said recombinant expression construct comprising said NLS from the cell.

In a further embodiment, the invention provides a method for detecting proteins or fragments thereof containing one or more nuclear localization sequence. In the practice of this aspect of the invention, cDNAs encoding proteins containing a NLS are fused to Gal80p. The presence of an exogenous nuclear localization sequence in said protein results in sequestration of Gal80p in the nucleus and limits export of Gal80p to the cytoplasm. In the nucleus, Gal80p inhibits Gal4p-mediated gene expression. Preferably, expression Gal4-mediated gene expression imposes a growth disadvantage on said cells, to that cells comprising said GAL80p-NLS fusion have a growth advantage. In preferred embodiments, NLS containing cells are detected by contacting yeast cells comprising URA3 operably linked with a GAL gene promoter with galactose and 5-FOA.

In a preferred embodiment, "host cells" are preferably yeast cells, and most preferably *Saccharomyces cerevisiae* cells. The recombinant expression constructs of the invention are preferably introduced into *Saccharomyces cerevisiae* cells. Alternatively, the recombinant expression constructs of the invention are introduced into other species within the genus *Saccharomyces*. Other species, strains, and varieties of yeast, such as *Pichia pastoris* and *Kluyveromyces lactis* are advantageous host cells for the recombinant expression constructs of the invention. The use of these varieties for such purposes is well known in the art. (See, Wolf, 1996, *Nonconventional Yeasts in Biotechnology*, Springer-Verlag: Berlin.) Yeast useful in the practice of the methods of the invention include but are not limited to *S. carlsbergensis, S. diastaticus, S. oviformis, S. norbensis, S. rouxii*, and *Kluyveromyces lactis*. Preferably the host yeast cells used according to the methods of the present invention carry mutations in their chromosomal genes for one of more of a multiplicity of selectable markers encoded by recombinant expression construct. In preferred embodiments, the yeast cells have inactivating mutations in the HIS3, TRP1, or URA3 genes. In one preferred embodiment, the host yeast cells used according to the methods for detecting protein—protein interactions are chromosomally defective for Gal3p and Gal80p and are preferably of the ScGP786 strain. In another preferred embodiment, the host yeast cells used according to the methods for NES selection are chromosomally defective for Gal80p. In yet other preferred embodiments, the host yeast cells used according to the methods for NLS selection are chromosomally defective for Gal80p. In a further embodiment, recombinant expression constructs encoding Gal80p fusion proteins are introduced into one of a multiplicity of host yeast cells that satisfy the above requirements.

The methods and reagents of the invention can be used to induce galactose-independent GAL gene expression. Cells harboring two proteins with one fused to Gal80p and the other fused to a membrane targeting sequence are treated with an induction agent to induce protein—protein interaction. The association of the proteins traps Gal80p in the cytoplasm permitting transcriptional activation of GAL gene promoters and the expression of genes fused to those promoters.

The following Examples illustrate certain aspects of the above-described invention and advantageous results thereof. The following examples are shown by way of illustration and not by way of limitation. The disclosure of each reference cited herein is explicitly incorporated by reference.

EXAMPLE 1

Preparation of Plasmids Containing Membrane Targeting Sequences and Localization of Fusion Protein Expression To determine if Gal80p would interact with membrane-bound proteins, Gal80p's natural binding partner, Gal3p was tethered to the cell and mitochondrial membranes. In addition, the effects of Gal3p sequestration on galactose induction of GAL gene expression were examined.

Gal3p was targeted to the cytoplasmic or mitochondrial outer membranes by fusion to a protein myristoylation signal (Myr-Gal3p) or mitochondrial outer membrane signal anchor sequence (MOM-Gal3p), respectively. N-myristoylation (Johnson et al., 1994, *Annu. Rev. Biochem.* 63: 869–914; Resh et al., 1999, *Biochem. Biophys. Acta.* 1451: 1–16) was chosen because it is a co-translational process that occurs when the nascent peptide is still attached to the ribosome. Mitochondria targeting was chosen because it appears to be a very fast and efficient process (Fujiki and Verner, 1993, *J. Biol. Chem.* 268: 1914–20; Funfschilling et al., 1999, *Mol. Biol. Cell.* 10: 3289–99).

Gal3p derivatives bearing protein N-myristoylation signals were generated by inserting oligonucleotides encoding each signal peptide sequence into GAL3 gene at the N terminus. The N-myristoylation signals used herein are: MGCTVSTQTIGDESDP (SEQ ID NO:1), obtained from the N-terminal domain of Gpa1p (a G protein α subunit), a N-myristoylation signal variant MACTVSTQTIGDESDP (SEQ ID NO:2) (the single G→A substitution abolishes the acylation and membrane targeting), or the mitochondria outer membrane signal anchor sequence (the first 29 amino acid residues of Tom70p (MKSFITRNKTAILATVAATGTAIGAYYYY (SEQ ID NO:3)), a component of the translocase of the outer mitochondrial membrane complex). It has been shown that the N-myristoylation signal used here is sufficient to target a heterologous protein to the plasma membrane (Gilen et al., 1992, *J. Cell. Sci.* 111: 3235–44). The first 29 amino acids of Tom70p protein is sufficient to target a heterologous protein to the outer membrane of mitochondria, leaving the bulk of protein extruding into the cytoplasm (McBride et al., 1992, *J. Cell. Biol* 119: 1451–1457). The ADH2 promoter, FPR1, CNA1, HOM3 and CMD1 sequences were PCR amplified using yeast Sc723 genomic DNA as the template and oligonucleotide primers disclosed in the Examples below. Green fluorescence protein (GFP) and cyan fluorescence protein (CFP) sequences were PCR amplified using pYGFP1 (Cormack et al., 1996, *Gene* 173: 33–38) and pDH3 (Yeast Resource Center, University of Washington) as template, respectively.

Plasmid constructions to generate the Myr-Gal3, mMyr-Gal3 and MOM-Gal3 plasmids were prepared as follows. Myr-Gal3 and mMyr-Gal3 fusions were constructed in plasmid pTEB16, a low-copy number yeast shuttling plasmid having a TRP1 marker (Blank et al. 1997, *Mol Cell Biol.* 17: 2566–75). A SpeI site and a PstI site were created at the N terminus of GAL3 in pTEB16 (Peng and Hopper, 2000, *Molec. Cell Biol.* 20: 5140–8). The oligonucleotides GANG49/50 encoding MGCTVSTQTIGDESDP (SEQ ID NO: 1) were annealed and inserted at SpeI/PstI site to generate Myr-Gal3 construct. An identical procedure was used to create a mMyr-Gal3 bearing plasmid. The MOM-Gal3 plasmid (containing MOM targeting sequence, HA tag, GFP and GAL3) was constructed in plasmid pTEB16, a low-copy number yeast shuttling plasmid having a TRP1 marker (Blank et al., 1997, *Mol. Cell. Biol.* 17: 2566–75). A SpeI site and a PstI site were created at the N terminus of GAL3 in pTEB16 (Peng and Hopper, 2000, *Mol. Cell. Biol.* 20: 5140–8). The oligonucleotides GANG53/55 and GANG54/56 were annealed separately and then inserted at SpeI/PstI site to add the MOM targeting sequence. The oligonucleotides GANG59/60 were annealed and inserted at the PstI site to add the hemagluttinin (HA) tag. The PCR product using pYGFP1 (Cormack et al., 1996, *Gene* 173: 33–8) as template and GANG31/61 as primers was cut with PstI and inserted at PstI site to add the GFP sequence.

The oligonucleotides and the references relating to the constructions of the Myr-Gal3, mMyr-Gal3 and MOM-Gal3 plasmids are provided below.

TABLE 1

Oligonucleotide Primers

| | | |
|---|---|---|
| GANG31 (SEQ ID NO:7) | PstI-GFP foward | AAC TGC AGG TAT GTC TAA AGG TGA AG |
| GANG49 (SEQ ID NO:8) | myr/palm signal-1 | CTA GTA TGG GGT GTA CAG TGA GTA CGC AAA CAA TAG GAG ACG AAA GTG ATC CTT CTG CA |
| GANG50 (SEQ ID NO:9) | myr/palm signal-2 | GAA GGA TCA CTT TCG TCT CCT ATT GTT TGC GTA CTC ACT GTA CAC CCC ATA |
| GANG53 (SEQ ID NO:10) | Tom70(29)-1-sense | CTA GTA TGA AGA GCT TCA TTA CAA GGA ACA AGA CAG CCA TTT TGG CAA |
| GANG54 (SEQ ID NO:11) | Tom70(29)-2-sense | CCG TTG CTG CTA CAG GTA CTG CCA TCG GTG CCT ACT ATT ATT ACG GTG CTG CA |
| GANG55 (SEQ ID NO:12) | Tom70(29)-1-antisense | GCA ACG GTT GCC AAA ATG GCT GTC TTG TTC CTT GTA ATG AAG CTC TTC ATA |
| GANG56 (SEQ ID NO:13) | Tom70(29)-2-antisense | GCA CCG TAA TAA TAG TAG GCA CCG ATG GCA GTA CCT GAT GCA |
| GNAG59 (SEQ ID NO:14) | Linker/HA for Tom70-3-sense | CAG TTG GGT GGT GGT GGT CGT TAC CCA TAC GAC GTC CCA GAC TAC GCT GCA |
| GANG60 (SEQ ID NO:15) | Linker/HA for Tom70-3-antisense | GCG TAG TCT GGG ACG TCG TAT GGG TAA CGA CCA CCA CCC AAC TGT GCA |
| GANG61 (SEQ ID NO:16) | PstI-GFP w/o stop | AAC TGC AGA TTT GTA CAA TTC ATC CAT AC |
| GANG113 (SEQ ID NO:35) | Cmd1-SphI/ClaI-forward | AAA AAA GTA CAg cat gca aAT GTC CTC CAA TCT TAC CGA AG |
| GANG114 (SEQ ID NO:36) | Cmd1-SphI/ClaI-reverse | GAT GCA CCT Aat cga ttT TTA GAT AAC AAA GCA GCG AAT TG |

After addition of these respective targeting signals, Myr-Gal3p expressed using these constructs localized to the plasma membrane and MOM-Gal3p expressed using these constructs localized to the mitochondria. In contrast, wild type Gal3p was shown to be located throughout the cytoplasm, as was Gal3p joined to the variant N-myristoylation signal having a single amino acid substitution that cannot be acylated. These results are shown in FIG. 1A. The expression patterns of Myr-Gal3p and MOM-Gal3p were examined by fluorescence microscopy using a Nikon Optiphot-2 epifluorescence microscope equipped with a 100× objective. GFP was excited and its emission fluorescence was detected using Chroma filter # 41017 (Chroma Technology Corp., Brattleboro, Vt.). Images were acquired using a SenSys KF1400 CCD camera (Photometrics Ltd, Tucson, Ariz.), controlled by QED (Pittsburgh, Pa.) software.

Thus, fusion of Gal3p to membrane targeting sequences resulted in appropriate localization of Gal3p at the cell and mitochondrial membranes.

EXAMPLE 2

Membrane Associated Gal3p Retains Ability to Bind Gal80p and Induce GAL Gene Expression To verify appropriate activity of Myr-Gal3p or MOM-Gal3p in yeast cells harboring the plasmids encoding these fusion proteins, semi-quantitative colony growth assays and galactose-responsive reporter gene analyses were performed. Following verification of appropriate Gal3p expression, the distribution of Gal80p in Myr-Gal3p or MOM-Gal3p expressing cells was examined by fluorescence microscopy and Western blot analysis.

Gene expression was determined for two different types of GAL gene promoters in cells carrying the membrane bound and cytoplasm sequestered Gal3p. First, a sensitive and semi-quantitative colony growth assay was used to assess expression of a HIS3 reporter gene whose promoter bears four UAS$_{GAL}$ sites. Cells of a gal3Δgal1Δ strain (Sc781) carrying Myr-Gal3p or MOM-Gal3p grew indistinguishably from cells harboring wild type Gal3p on synthetic medium lacking histidine in these assays. Because growth rates are proportional to the level of HIS3 gene expression and HIS3 gene expression is proportional to the level of Gal3p activity, we concluded that Myr-Gal3p and MOM-Gal3p are as active as native Gal3p (data not shown). Second, expression of MEL1, a galactose-responsive gene whose promoter bears a single UAS$_{GAL}$ site was quantified. See Lazo et al., 1977, *Eur. J. Biochem.* 77: 375–382; Buckholz and Adams, 1981, *Molec. Gen. Genet.* 182: 77–81; Post-Beittenmiller et al., 1984, *Molec. Cell Biol.* 4: 1238–1245.

Despite effective sequestration of Gal3p to the cell cytoplasmic membranes, the MEL1 gene was expressed up to wild type levels upon galactose induction (these results are shown in FIG. 1B). The level of MEL1-encoded α-galactosidase in the extracts of cells carrying Myr-Gal3p was not significantly different from that detected in extracts of cells carrying wild type Gal3p (p>0.1, Student's t-test), or carrying a mMyr-Gal3p variant that abolished plasma association (p>0.1). The mitochondria associated Gal3p (MOM-Gal3p) gave rise to higher MEL1 expression than the wild type Gal3p did (p<0.05). Using Western analyses, it was found that membrane association of Gal3p did not increase steady state levels of Gal3p. Cellular levels of Myr-Gal3p and the mMyr-Gal3p variant were slightly lower than that of wild type Gal3p, while the MOM-Gal3p level was similar to that of wild type Gal3p (data not shown). Thus, Myr-Gal3p, mMyr-Gal3p and MOM-Gal3p are all synthesized to similar levels.

Several lines of evidence indicated that the full induction of GAL genes observed in cells harboring membrane-bound Gal3p was due to the interaction between Gal3p and Gal80p at the cytoplasmic membranes. First, the targeting methods employed were very effective in sequestering Gal3p to the membranes. Based on cell fractionation and Western analyses, essentially all the Gal3p in these cells was associated with the membrane when expressed joined to a myristoylation signal. For the mitochondria-targeted Gal3p, less than about 10% of MOM-Gal3p was found in the soluble cytoplasmic fraction (data not shown). Second, Gal80p redistributed to the plasma membrane and the intracellular vesicle membrane in cells expressing Myr-Gal3p (shown in FIG. 1C). Lastly, a small fraction of Gal3p that might have escaped the cytoplasmic sequestering methods used herein would not have been sufficient to give rise to the levels of GAL gene expression observed in these experiments (shown in FIG. 2). Three plasmids providing different subcellular locations and expression levels of Gal3p were constructed and expression levels of the MEL1 gene in cells carrying these plasmids were determined. The results showed that a five-fold reduction of Gal3p resulted in a two-fold reduction in MEL1 gene expression level, indicating that Gal3p is not in large excess in the cells and that quantitative interactions between Gal3p and Gal80p are required for the transcription of GAL genes. In comparison, a two-fold reduction of Gal3p derivative was observed in cells carrying Myr-Gal3p and resulted in 20% reduction in MEL1 gene expression level.

In summary, these results demonstrated that Gal3p maintains its induction function and its induction capacity and that active transcription of GAL genes in cells harboring Myr-Gal3p is due to the Gal3p-Gal80p interaction at the plasma and vesicular membranes outside the nucleus, rather than to Gal3p interaction with the Gal80p-Gal4p complex in the nucleus. Additionally, the interaction between Gal80p and membrane bound Gal3p resulted in the appropriate activation of GAL reporter gene expression within the nucleus.

EXAMPLE 3

Gal80p Association with Gal4p within Gene Promoters is Reduced

Because the association of Gal80p with Gal4p at a GAL gene promoter is essential for inhibition of Gal4p in the absence of galactose, the effect of galactose (which triggers the interaction between Gal3p and Gal80p) on the amount of Gal80p complexed with DNA-bound Gal4p was determined (Torchia et al., 1984, Mol. Cell Biol. 4: 1521–1527; Lohr et al., 1987, J. Biol. Chem. 262: 15589–15597). To determine the extent of Gal4p and Gal80p association with the UAS$_{GAL}$ region of the GAL1/GAL10 gene promoter, formaldehyde-based in vivo cross-linking assays were performed followed by chromatin immunoprecipitation.

Chromatin immunoprecipitations were performed as described by Braunstein et al., 1993, Genes Dev. 7: 592–604 and Kuras et al. 1999, Nature 399: 609–613. Briefly, wild type Sc723 cells (Blank et al., 1997, Mol. Cell. Biol. 17: 2566–2575) were grown to early exponential growth phase (as measured by absorbance at 600 nm ~0.4) in 250 mL yeast extract-peptone medium containing 2% glycerol, 3% lactic acid, and 0.05% glucose (-galactose, un-induced). For galactose-induced cultures, galactose was added to the un-induced cultures to a final concentration of 2% and the cultures-were incubated for an additional 20 minutes. Formaldehyde was added to a final concentration of 1%, the cultures were incubated for 20 minutes at room temperature, and glycine was added to a final concentration of 300 mM. All the following steps were carried out at 4° C. Cells were washed twice with TBS (20 mM Tris-HCl, 150 mM NaCl, pH 8.0), resuspended in 1 mL lysis buffer (50 mM Tris-HCl pH 8.0, 10 mM EDTA, 1% SDS, 1 mM PMSF), and disrupted by vortexing with glass beads. The cross-linked chromatin was pelleted by centrifugation at 200,000 g for 12 minutes, resuspended in 1 mL lysis buffer, and sonicated to yield DNA fragments of 300 base pairs average size. Soluble chromatin was separated from insoluble materials by centrifugation at 13,000 g for 15 minutes. Finally, the volume of soluble chromatin was adjusted to 10 mL with dilution buffer (16.7 mM Tris-HCl, pH 8.0, 16.7 mM NaCl, 1.2 mM EDTA, 0.01% SDS, 1.1% Triton-X100, 1 mM PMSF) and the resultant chromatin solution was stored in 1 mL aliquots at −80° C. For immunoprecipitation assays, 5 µL rabbit anti-Gal4p serum, 5 µL anti-Gal80p serum, or 5 µL anti-Gal3p serum was added to 1 mL chromatin solution. After overnight incubation on a rotator, 75 µL of protein-A-Sepharose beads were added, and the reactions were incubated for two more hours. Precipitated protein-DNA complexes were eluted from the beads, cross-linked reversed, treated with proteinase K, and analyzed by quantitative radioactive PCR using primer pairs GANG67/68 for the UAS$_{GAL}$ region and GANG71/72 for an intergenic control region located 5 kb downstream from the GAL1 gene. The sequences of the primers were GANG67: CATGGCATTAC-CACCATATACATATCC (SEQ ID NO:17); GANG68: GAAGGTTTGTGGGGCCAGGTTACTGC (SEQ ID NO:18); GANG71: GTGCATTTGGCCTTCAATGAGC (SEQ ID NO: 19); GANG72: AAGTGATGTTCGACAT-ACCTGTAAC (SEQ ID NO:20). A dilution (1/30,000) of input DNA, 1/200 of anti-Gal4p antibody precipitated DNA, 1/50 of anti-Gal80p antibody precipitated DNA, and 1/25 of anti-Gal3p antibody precipitated DNA were used as template for the various reactions. PCR conditions were as follows: 0.5 µM each primer, 0.25 mM each dNTP, 1.5 mM MgCl$_2$, 0.06 mCi/mL {α-$^{32}$P}dATP in a 20 µL reaction volume. PCR cycle regimen was as follows: 3 minutes at 94° C., followed by 25 cycles of 1 minute at 94° C., 1 minute at 52° C., and 1 minute at 72° C. PCR products were resolved on 8% polyacrylamide gels in 1× TBE buffer. Quantitation of incorporated {α-$^{32}$P}dATP in the PCR products was performed using a PhosphorImager (Molecular Dynamics) analysis.

Because Gal80p is associated with the UAS$_{GAL}$ solely through its binding to Gal4p, comparison of the amount of the UAS$_{GAL}$ DNA associated with Gal4p and Gal80p provided an assessment of the interaction between Gal4p and Gal80p. It was found that, while Gal4p occupancy of the UAS$_{GAL}$ site slightly increased upon galactose signaling, the Gal80p association with the UAS$_{GAL}$ region decreased significantly. Repeated trials did not yield any evidence that Gal3p is associated with the GAL1/10 gene promoter (results shown in FIG. 3). These data indicated that concurrent with galactose-induced interaction between Gal3p and Gal80p in the cytoplasm, the association between Gal80p and UAS$_{GAL}$-bound Gal4p decreases in the nucleus.

EXAMPLE 4

GAL Gene Expression Activated by Surrogate Protein—Protein Interactions in the Cytoplasm: The 80-Trap The results shown in Examples 1–3 above indicated that the galactose-triggered Gal3p-Gal80p interaction traps Gal80p in the cytoplasm, thereby causing the observed removal of Gal80p from the promoters of GAL genes and activation of Gal4p. The behavior of the Gal80p-Gal3p interaction in vivo is consistent with this view, as the membrane-bound Myr-Gal3p is shown to sequester Gal80p to the membranes where Myr-Gal3p is located (as shown in FIG. 1C).

Given the new insights into the activation of Gal4p shown here, a method for trapping Gal80p in the cytoplasm was developed for use as an assay to detect protein—protein interactions in the cytoplasm and/or nuclear export/localization sequences and to regulate Gal4p-activation of GAL gene promoters by small molecules other than galactose. In this method, termed the 80-Trap method, a specific bait protein (identified as a known protein of interest) is fused to Gal80p to create a fusion protein with Gal80 at either the amino- or carboxyl-terminus of Gal80p. The bait protein's binding partner, prey protein (either another known protein of interest or a multiplicity of yet unidentified potential partners encoded in a cDNA library), is tethered to the cell or mitochondrial outer membrane via fusion to membrane targeting sequences (myristoylation or mitochondrial Tom70 sequence, respectively). If the bait and prey proteins interact in the cytoplasm, Gal80 is trapped in the cytoplasm and prevented from inhibiting Gal4p-mediated transcriptional activation of GAL gene promoters in the nucleus.

Using this method, it was expected that substituting Gal3p with a surrogate-binding factor for Gal80p in the cytoplasm would activate GAL gene expression. To test this possibility, the interaction between Fpr1p and Can1p that is elicited by a small membrane-permeable molecule FK506, a macrolide isolated from *Streptomyces tsukubaensis* (Kino et al., 1987, *J Antibiot* (Tokyo) 40: 1249–1255; Liu et al., 1991, *Cell* 66: 807–815; Cardenas et al., 1995, *Embo J* 14: 2772–2783; and Griffith et al., 1995, *Cell* 82: 507–522) was used. Expression constructs and production of yeast strain ScGP786 was as is described below.

pGP82 (Gal80-Fpr1) is made up of nucleotide sequences encoding a GAL80, 2 HA tags, and FPR1 on a pRS416 (Sikorski and Hieter, 1989, *Genetics* 122: 19–27) backbone. GAL80 sequence was obtained from yeast genomic clones using polymerase chain reaction, and having the sequence disclosed at http://genome-www4.stanford.edu/egi-bin/SGD/locus.pl?locus=gal80. HA was derived from oligonucleotides GANG33/34. FPR1 was the ClaI digested PCR product generated by using yeast genomic DNA as template and GANG117/118 as primers. pGP130 (Myr-Hom3) contains an ADH2 promoter, CFP sequence, and HOM3 sequence on a pRS424 (Sikorski and Hieter, 1989, *Genetics* 122: 19–27) backbone. The ADH2 promoter was the PCR product using yeast genomic DNA as template and GANG83/84 as primers. CFP was the PCR product using pDH3 as template (Yeast Resource Center, University of Washington) and GANG101/112 as primers. HOM3 was a PCR product using yeast genomic DNA as template and GANG125/126 as amplification primers. pGP139 (Myr-Cna1) contains an ADH2 promoter, CFP sequence, and CNA1 sequence. An ADH2 promoter was obtained as a PCR product using yeast genomic DNA as template and GANG83/84 as primers. CFP was obtained as a PCR product using pDH3 as template (Yeast Resource Center, University of Washington) and GANG101/112 as primers. CNA1 was obtained from a PCR product using yeast genomic DNA as the template and GANG141/142 as primers.

ScGP786 was derived from Sc786 (Blank et al., 1997, *Mol. Cell. Biol.* 17: 2566–2575). For the replacement of FPR1 gene with ADE1, ADE1 ORF under control of a GAL1/10 gene promoter was cloned into plasmid pUG6 carrying the dominant Kan' gene (Guldener et al., 1996, *Nucleic Acids Research* 24: 2519–2524). Yeast cells were transformed by the PCR product from the reaction using oligonucleotide primers GANG 119/120 with 45 bp homology to FPR1 chromosomal locus at 33 nt upstream and 33 nt downstream. Transformation and homologous recombination events were selected by plating cells on YPD plates containing 200 mg/L Geneticin (G-418 sulphate).

FK506 was used to trigger the interaction between a Gal80-Fpr1p fusion and plasma membrane-localized Myr-Can1p. It has been shown that FK506 by itself does not activate transcription of the GAL genes (Biggar and Crabtree 2001, *Embo. J.* 20:3167–3176). Induction of the galactose-inducible HIS3 reporter gene was assayed. Cells of a gal80Δ gal3Δ gal1Δ strain (ScGP786) carrying both Gal80-Fpr1 and Myr-Can1p plasmids exhibited evident growth only on the plate containing FK506 (shown in FIG. 4A). It has been reported that Fpr1p also interacts with Hom3p, the aspartokinase, in the absence of FK506 in a yeast two-hybrid assay (Alarcon and Heitman, 1997, *Mol. Cell Bio.,* 17: 5968–5975). Following a scheme that paralleled the one above, it was found that the heterologous interaction between Gal80-Fpr1p and Myr-Hom3p was able to activate HIS3 reporter gene expression (shown in FIG. 4B). It was also determined by the Western analyses that the Gal80-Fpr1p fusion was present at a slightly higher level in cells containing both Gal80-Fpr1p and Myr-Hom3p as compared to cells harboring the non-interacting controls, Gal80-Fpr1p and Myr-Cmd1p, indicating that activation of the HIS3 reporter gene was not due to the degradation of Gal80-Fpr1p in cells expressing Myr-Hom3p.

The above results demonstrated that Gal4p-mediated gene expression may be activated by the cytoplasmic interaction of surrogate proteins. Thus, the potential interaction between proteins of interest and uncharacterized cDNAs may be detected with this novel cytoplasmic based system. In addition to the 'forward' two-hybrid modes described above, the system may also be used effectively in the 'reverse' two-hybrid mode (analogous to the use of the conventional two hybrid system as shown in Vidal et al., 1996, *Proc. Natl. Acad. Sci. USA* 93:10315–20). The 80-Trap system may select for loss of interaction mutations in either cDNA (bait or prey) and provides a method for identifying and mapping the amino acids involved in protein—protein interaction.

EXAMPLE 5

Detecting Transcriptional Proteins Interactions With The 80-Trap Method

Figure 6:
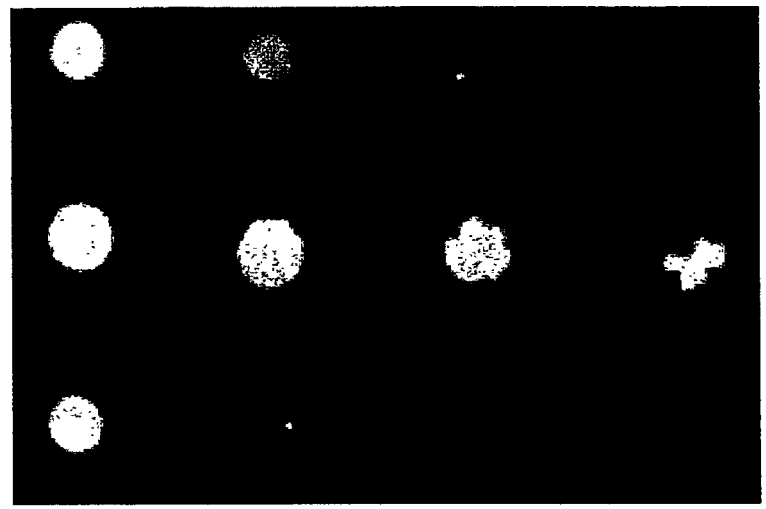
FIG. 6. A membrane-targeted transcription factor activates GAL gene expression through interaction with Gal80-TBP. Galactose-independent HIS3 reporter (expression as a result of Gal80-TBP and Myr-TAF145 interaction (lane 1)). The nutrient agar plate used here contained 3% glycerol/2% lactic acid as carbon source and lacked histidine, tryptophan and uracil.

In conventional yeast two-hybrid methods, transcriptional activator proteins can activate two-hybrid reporters through either direct binding to the RNA polymerase or through binding to other proteins that in turn bind to an RNA polymerase subunit. The protein interactions for the 80-Trap occur in the cytoplasm and would thus circumvent the false activation of GAL promoters. To examine the actions of transcriptional proteins in the 80-Trap system, the transcriptional protein, TATA binding protein (TBP), was fused to Gal80 p. The N-terminal domain (amino acids 1–71) of TAF145 was fused to the myristoylation sequence. TAF145 and TBP are established components of the transcriptional machinery and are known to interact via protein—protein interactions (Kokubo, et al., 1998, *Mol. Cell. Biol.* 189: 1003–1012). Heterologous interaction between the Gal80-TBP and Myr-TAF145 was able to activate the HIS3 reporter gene expression (shown in FIG. 6, line 1).

Figure 7:
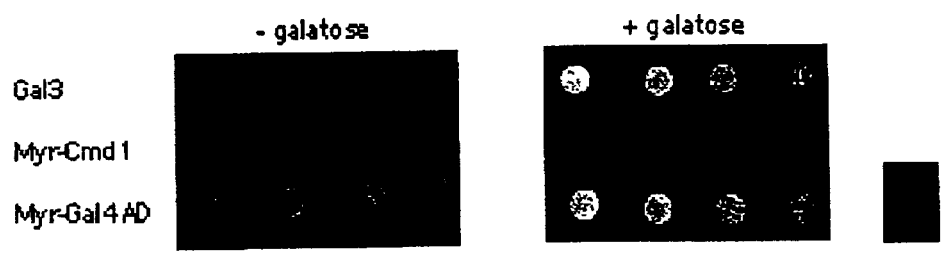
FIG. 7. Membrane targeted transcriptional activation domain of Gal4p (Gal4AD; a.a. 758–881) activates HIS3 reporter gene expression. A yeast strain harboring a $UAS_{GAL}$-HIS3 reporter was transformed with Myr-Gal4AD. The photomicrograph on the right shows the membrane localization of Myr-Gal4AD in yeast cells. Transformed cells were spotted on synthetic medium plates lacking histidine, tryptophan and uracil and containing 3% glycerol/2% lactic acid as carbon source. Cells showed evident growth in the absence of galactose, indicating an interaction between membrane-localized Gal4AD and Gal80p caused activation of the HIS3 reporter gene. As controls, cells carrying Gal3p exhibited growth only in the presence of galactose.

In a subsequent study, the transcription activation domain (AD) of Gal4p was tethered to the cell membrane by fusion to the myristoylation signal. Cells harboring the Myr-Gal4 (AD) fusion deplete GAL80p from the nucleus and in turn permitted the native Gal4p to activate transcription of GAL reporter genes (as shown in FIG. 7). Similarly, tethering of any one of a multiplicity of other transcription activation domains outside of the nucleus and its interaction with a binding partner fused to Gal80p would result in reporter gene activation.

These results demonstrated that transcription factors, and transcription activator domains may be tethered to the cells plasma and vesicular membranes or mitochondrial outer membrane and used to accurately screen for potential protein—protein interactions. This method permits the study of protein interactions not suitable for conventional two-hybrid approach. Because protein interactions occur in the cytoplasm, the potential for false activation of reporter genes is reduced, and the potential for detecting protein interactions when one or both of the proteins require a cytoplasmic location is optimized.

TABLE 2

Oligonucleotide Primers

| | |
|---|---|
| GANG33 (SEQ ID NO:21) | CGT TAC CCA TAC GAC GTC CCA GAC TAC GCT GGT TGG |
| GANG34 (SEQ ID NO:22) | CGC CAA CCA GCG TAG TCT GGG ACG TCG TAT GGG TAA |
| GANG83 (SEQ ID NO:23) | GAT ACT TCC CAA TTC GTC TTC AGA G |
| GANG84 (SEQ ID NO:24) | CTG GAA TAG ACT AGT TGT GTA TTA CGA TAT AG |
| GANG101 (SEQ ID NO:25) | CCA ATG CAT GTA TGA GTA AAG GAG AAG AAC TTT TCA C |
| GANG113 (SEQ ID NO:35) | AAA AAA GTA CAg cat gca aAT GTC CTC CAA TCT TAC CGA AG |
| GANG114 (SEQ ID NO:36) | GAT GCA CCT Aat cga ttT TTA GAT AAC AAA GCA GCG AAT TG |
| GANG112 (SEQ ID NO:26) | TTT GTA TTg CAT gcg gac cGG GGA TC |
| GANG117 (SEQ ID NO:27) | ACA AGT AAT Aat cga tcg TCT GAA GTA ATT GAA GGT AAC |
| GANG118 (SEQ ID NO:28) | TTT GCT TTT Aat cga ttG TTG ACC TTC AAC AAT TC |
| GANG119 (SEQ ID NO:29) | ATA AAC TCG TGA AAG CTT AAA GTA AGG CCT TTC ACC TAA ACT CGA GTC GTT AGA ACG CGG CTA C |
| GANG120 (SEQ ID NO:30) | TCA ATT AAG GCT CAG ATA CTT ACC ATA AAC ATA AAT AAA AAG CAG TCA CTA TAG GGA GAC CGG CAG |
| GANG125 (SEQ ID NO:31) | TTT AAC TTT TAC gca tgc aaA TGC CAA TGG ATT TCC AAC CTA C |
| GANG126 (SEQ ID NO:32) | GGT GGA TTT Agg cgc ctA ATT CCA AGT CTT TTC AAT TGT TC |
| GANG141 (SEQ ID NO:33) | CAA CGC CAg cAT Gct gTC GAA AGA CTT GAA TTC TTC ACG C |
| GANG142 (SEQ ID NO:34) | GTG CTT AGa tcg att aCG TTT CAT TCA AAC CTT CAG TCC C |

EXAMPLE 6

Figure 8:
FIG. 8. Addition of exogenous nuclear export sequence (NES) to Gal80p causes increased Gal4p-mediated reporter gene activation. Fusion of an NES to Gal80p increases Gal4p activation of a reporter gene in response to low levels of galactose. Top row, $P_{Ga80}$-Gal80-NES. 2. Middle row, $P_{Ga80}$-Gal80. 3. Bottom row, Gal80-deletion. The host yeast strain: Sc725 (ura3⁻, trp1⁻, his3⁻, gal80Δ). Growth of yeast on agar lacking uracil and histidine and containing 10 mM 3-Azotriazole (to eliminate leaky HIS3 expression) and carbon sources 3% glycerol, 2% lactic acid, 0.02% glucose and 0.1% galactose. Photo taken 7 days after spotting.

Detection of Nuclear Export Sequences and Nuclear Localization Sequence by Fusion to Gal80p In addition to measuring protein—protein interactions, the methods of the present invention are useful for detecting peptides containing nuclear export or nuclear localization sequences. For detecting nuclear export sequences, Gal80p is fused to a cDNA or one or a plurality of members of a cDNA library. cDNAs encoding peptides containing a nuclear export sequence (NES) sequester Gal80p to the cytoplasm. This in turn permits Gal4p-mediated transcriptional activation of GAL gene promoters in the presence of 0.01% galactose, a level normally not sufficient to permit Gal4p-mediated transcriptional activation of GAL gene promoters. (shown in FIG. 8).

For detecting nuclear localization sequences, cDNAs encoding proteins containing an NLS sequence are fused to Gal80p. The presence of an exogenous nuclear localization sequence in said protein results in sequestration of Gal80p in the nucleus and prohibits export of Gal80p to the cytoplasm, resulting in the inability to bind to Gal3p in the cytoplasm when galactose is present. This inability of Gal80p to exit from the nucleus and bind to Gal3p allows Gal80p to maintain its high concentration in the nucleus and binding to Gal4p and prevents Gal4p-mediated activation of genes whose expression is regulated by galactose and Gal4p. In yeast cells harboring a Ura3 gene expressed from a GAL gene promoter, said fusion of an NLS sequence to Gal80p prevents the URA3 enzyme from being produced and consequently protects the cell from the toxic effects of 5-FOA. The yeast cells harboring said NLS-Gal80p fusion thus grow as colonies on nutrient agar containing 3% glycerol/2% lactic acid, 0.1% galactose as carbon source and 5-FOA. In summary, the methods of the present invention provide a means for detecting both nuclear export and nuclear localization sequences.

It should be understood that the foregoing disclosure emphasizes certain specific embodiments of the invention and that all modifications or alternatives equivalent thereto are within the spirit and scope of the invention as set forth the appended claims.

We claim:

1. A method for detecting protein—protein interactions in a host cell cytoplasm by detecting transcriptional activation of a gene operably linked to a promoter sensitive to or transcriptionally inhibited by a transcription inhibitor, the method comprising the steps of:
   a) introducing a first recombinant expression construct encoding a first protein or protein-binding fragment thereof fused with the amino- or carboxyl-terminus of a transcriptional inhibitor;
   b) introducing a second recombinant expression construct encoding a second protein or protein-binding fragment thereof fused to a cytoplasm localization sequence, wherein upon interaction of the first and second proteins in the cell cytoplasm, said transcriptional inhibitor is localized to the cytoplasm, wherein transcription of a gene operably linked to a promoter that is sensitive to or regulated by said transcriptional inhibitor is increased; and
   c) detecting said increased transcription of said gene wherein said protein—protein interaction is detected thereby.

2. The method of claim 1 wherein the first protein is a protein encoded by a cDNA or a member of a cDNA library.

3. The method of claim 1 wherein the first protein is a transcriptional activator protein or one of a multiplicity of proteins that participate in protein—protein interactions to bring about transcriptional activation.

4. The method of claim 1 wherein the second protein is a protein encoded by a cDNA or a member of a cDNA library.

5. The method of claim 1 wherein the second protein is a transcriptional activator protein or one of a multiplicity of proteins that participate in protein—protein interactions to bring about transcriptional activation.

6. The method of claim 1 wherein said first or second proteins are detectable or produce detectable metabolites.

7. A method according to claim 1, wherein the gene operably linked to a promoter that is sensitive to or regulated by said transcriptional inhibitor is a selectable gene, wherein increased expression of said gene confers a growth advantage on the cell.

8. The method of claim 1 wherein the cytoplasm localization sequence is a membrane targeting sequence.

9. The method of claim 8 wherein the membrane targeting sequences are a myristoylation sequence, mitochondrial outer membrane targeting sequence, or a membrane anchoring sequence.

10. The method of claim 9 wherein the myristoylation sequence is MGCTVSTQTIGDESDP (SEQ ID NO:1).

11. The method of claim 9 wherein the mitochondrial outer membrane targeting sequence is the N-terminal sequence of the Tom70/Mas70 protein, MKSFITRNKTAIL-ATVAATGTAIGAYYYY (SEQ ID NO:3).

12. The method of claim 1 wherein the gene operably linked to a promoter that is sensitive to or regulated by said transcriptional inhibitor is a gene expressed from an activated yeast GAL gene promoter.

13. The method of claim 12 wherein the genes expressed from the GAL gene promoters are HIS3, URA3, TRP1, ADE2, ADE5, ADE7, LYS2, KAN$^R$, or one of a multiplicity of genes whose encoded protein provides the cell with the ability to grow under selection conditions.

14. The method of claim 12 wherein the GAL gene promoter is a galactose-inducible UAS$_{GAL}$ promoter.

15. The method of claim 12 wherein the gene operably linked to a promoter that is sensitive to or regulated by said transcriptional inhibitor is an endogenous cellular gene encoding a detectable product.

16. The method of claim 14 wherein the gene is GAL1, GAL7, GAL10, GAL5/PGM2, FUR4, GCY1, LAP3/GAL6, MTH1, PCL10 or MEL1.

17. The method of claim 15 wherein gene operably linked to a promoter that is sensitive to or regulated by said transcriptional inhibitor is an exogenous reporter gene encoding a detectable product.

18. A method according to claim 12, wherein the transcription inhibitor is Gal80p.

19. A method according to claim 18, further comprising the steps of:
   d) subjecting the host cell to selective growth conditions, and e) detecting increased growth or survival of said cells under selective growth conditions, wherein said protein—protein interaction is detected thereby.

20. A method for isolating a first or a second fusion protein, the first fusion protein fused with a transcription inhibitor, the second fusion protein fused to a membrane targeting sequence, the method comprising the steps of:
   a) detecting increased expression of the gene operably linked to a promoter that is sensitive to or regulated by said transcription inhibitor and
   b) isolating said first or second fusion protein.

21. The method of claim 20, wherein said first or second fusion protein comprises one or a plurality of members of a cDNA library.

22. A method for detecting protein—protein interactions in a yeast host cell cytoplasm, the method comprising the steps of:

a) introducing a first recombinant expression construct encoding a first protein or protein-binding fragment thereof fused with the amino- or carboxyl-terminus of Gal80p;
   b) introducing a second recombinant expression construct encoding a second protein or protein-binding fragment thereof fused to a cytoplasm localization sequence, wherein upon interaction of the first and second proteins in the cell cytoplasm, said amino or carboxyl terminus of Gal80p is localized to the cytoplasm, wherein transcription of a gene operably linked to a promoter that is sensitive to or regulated by said amino- or carboxyl-terminus of Gal80p is increased; and
   c) detecting said increased transcription of said gene wherein said protein—protein interaction is detected thereby.

* * * * *

UNITED STATES PATENT AND TRADEMARK OFFICE
CERTIFICATE OF CORRECTION

| | | |
|---|---|---|
| PATENT NO. | : 6,878,524 B2 | Page 1 of 1 |
| APPLICATION NO. | : 10/165873 | |
| DATED | : April 12, 2005 | |
| INVENTOR(S) | : Peng et al. | |

It is certified that error appears in the above-identified patent and that said Letters Patent is hereby corrected as shown below:

At column 1, lines 10-12, delete:

"This application was supported by a grant from the National Institutes of Health, No. GM 27925. The government may have certain rights in this invention."

and replace it with:

-- This invention was made with government support Grant No. GM27925, awarded by The National Institutes of Health. The Government has certain rights in the invention. --

Signed and Sealed this

Twenty-fourth Day of May, 2011

David J. Kappos
*Director of the United States Patent and Trademark Office*